United States Patent
Xu et al.

(10) Patent No.: US 9,498,431 B2
(45) Date of Patent: Nov. 22, 2016

(54) CONTROLLED RELEASING COMPOSITION

(76) Inventors: Jianjian Xu, Hefei (CN); Shiliang Wang, Hefei (CN); Manzhi Ding, Hefei (CN)

( * ) Notice: Subject to any disclaimer, the term of this patent is extended or adjusted under 35 U.S.C. 154(b) by 0 days.

(21) Appl. No.: 13/133,656

(22) PCT Filed: Dec. 10, 2009

(86) PCT No.: PCT/CN2009/075468
§ 371 (c)(1),
(2), (4) Date: Jun. 9, 2011

(87) PCT Pub. No.: WO2010/066203
PCT Pub. Date: Jun. 17, 2010

(65) Prior Publication Data
US 2011/0244043 A1    Oct. 6, 2011

(30) Foreign Application Priority Data
Dec. 10, 2008 (CN) .......................... 2008 1 0182652

(51) Int. Cl.
| | |
|---|---|
| A61K 9/14 | (2006.01) |
| A61F 13/00 | (2006.01) |
| A61F 2/00 | (2006.01) |
| A61K 9/00 | (2006.01) |
| A61K 9/16 | (2006.01) |
| A61K 31/505 | (2006.01) |
| A61K 31/7036 | (2006.01) |
| A61K 45/06 | (2006.01) |
| A61K 9/20 | (2006.01) |

(52) U.S. Cl.
CPC ............ *A61K 9/0024* (2013.01); *A61K 9/1647* (2013.01); *A61K 9/1652* (2013.01); *A61K 9/1664* (2013.01); *A61K 31/505* (2013.01); *A61K 31/7036* (2013.01); *A61K 45/06* (2013.01); *A61K 9/204* (2013.01)

(58) Field of Classification Search
None
See application file for complete search history.

(56) References Cited

U.S. PATENT DOCUMENTS

| | | | |
|---|---|---|---|
| 5,522,895 A * | 6/1996 | Mikos .......................... 623/23.58 |
| 6,183,781 B1 | 2/2001 | Burke | |
| 7,053,134 B2 * | 5/2006 | Baldwin et al. ............... 522/154 |
| 2004/0058056 A1 * | 3/2004 | Osaki et al. .................... 427/2.1 |
| 2005/0037047 A1 | 2/2005 | Song | |
| 2007/0055364 A1 * | 3/2007 | Hossainy .................. A61F 2/82 |
| | | | 623/1.38 |
| 2008/0274194 A1 * | 11/2008 | Miller .................... A61K 9/146 |
| | | | 424/489 |

FOREIGN PATENT DOCUMENTS

| | | |
|---|---|---|
| CN | 1208610 A | 2/1999 |
| EP | 0251680 A2 | 1/1988 |
| JP | S63-22516 A | 1/1988 |
| JP | H10-310518 A | 11/1998 |
| WO | 96/10395 A1 | 4/1996 |
| WO | WO 2005000277 A1 * | 1/2005 |
| WO | 2007/115045 A2 | 10/2007 |
| WO | 2008/002657 A2 | 1/2008 |
| WO | 2008002657 A2 | 1/2008 |
| WO | 2008041246 A2 | 4/2008 |

OTHER PUBLICATIONS

Crowley and Zhang, Pharmaceutical Application of Hot Melt Extrusion: Part I, Drug Development and Industrial Pharmacy, 2007. 33:909-926.*
The Use of Poly (L-Lactide) and RGD Modified Microspheres as Cell Carriers in a Flow Intermittency Bioreactor for Tissue Engineering Cartilage. Biomaterials, 2006. 27:4453-4460.*
Lyu et al. Degradability of Polymers for Implantable Biomedical Devices. International Journal of Molecular Sciences, 2009. 10:4033-4065.*
Kang et al. The Effect of Microsphere Degradation Rate of the Efficacy of Polymeric Microspheres as Bulking Agents: An 18-Month Follow-up Study. Journal of Biomedical Materials Research Part B: Applied Biomaterials, 2007:253-259.*
Ikada, Yoshito. Challenges in Tissue Engineering. Journal of the Royal Society Interface, 2006. 3:589-601.*
"Written Opinion for PCT/CN2009/075468".

* cited by examiner

*Primary Examiner* — Maria Leavitt
*Assistant Examiner* — Kimberly A Aron
(74) *Attorney, Agent, or Firm* — Jun He Law Offices P.C.; James J. Zhu

(57) ABSTRACT

A controlled releasing composition comprising a plurality of microparticles and a matrix as well as the preparation method thereof is disclosed. The plurality of microparticles comprise a first material and the matrix comprises a second material. The melting temperature of the first material is higher than the melting temperature of the second material.

13 Claims, 15 Drawing Sheets

| Category and Name | | | Melting point/range | Remarks |
|---|---|---|---|---|
| Polysaccharide Biopolymers and Derivatives | Starch and Derivatives | Starch | | |
| | | Amylum pregelatinisatum | | |
| | | Dextrin | 178°C; Decomposition | |
| | | Cyclodextrins | | |
| | | Cross-linked starch | | |
| | | Hetastarch | | |
| | Cellulose and Derivatives | Microcrystalline Cellulose | | 260 ~ 270°C Carbonization |
| | | Methylcelulose | 190°C ~ 200°C | |
| | | Ethylcellulose | | |
| | | Cellulose Acetate | 230°C ~ 300°C | |
| | | Cellulose Acetate Phthalate(CAP) | | > 150°C Weight loss |
| | | Carboxymethyl Cellulose | | |
| | | Hydroxy Propyl Methylcellulose | | 190 ~ 200°C Discoloration |
| | | Hydroxypropylcellulose | | 130°C Softening |
| | | Hydroxypropyl Methyl Cellulose Phthalate | 150°C | |
| | | Hydroxypropyl Methylcellulose Acetate Succinate | | > 200°C Weight loss |
| | Acacia | | | |
| | Chitin, Chitosan and Derivatives | Chitin | | 270°C Degradation |
| | | Chitosan | | Tg 203°C |
| | | Deacetylated-chitosan | | |
| | Hyaluronic Acid | | | |
| | Alginate | | | |
| | Dextran | | | |
| | Tragacanth Gum | | | |
| | Xanthan Gum | | | 270°C Carbonization |
| Protein Biopolymers and Derivatives | Zein | | | 190°C |
| | Collagen | | | |
| | Gelatin | | | |
| | Albumin | | | |
| | Fibrinogen and Fibrin | | | |
| Shellac | | | | 115°C ~ 120°C |

FIGURE 1

| Category and Name | | | Melting point/range |
|---|---|---|---|
| Polyesters | Poly(lactic acid), Poly(glycolic acid) and Copolymers | Poly (L-lactic acid) | |
| | | Poly (DL-lactic acid) | |
| | | Poly(glycolic acid) | 225°C ~ 230°C |
| | | Poly(lactic-co-glycolic acid) | |
| | Polycaprolactone and Copolymers | Poly(ε-caprolacton) | 62°C |
| | | Copolymers of ε-caprolacton and lactide, glycolide, and (the) other lactone | |
| | Polyvalerolactone | | |
| | Poly(ε-decanolactone) | | |
| | Poly(ethylene glycol oxalate) | | 159°C |
| | Poly(β-malic acid) | | |
| | Poly(1,2-propylidene fumarate) | | |
| | Poly (ester ether) | | |
| | Polyesteramide | | |
| | Polyphosphate | | |
| | Poly(ether-urethane) | | |
| Polydioxanone and Copolymers | Polydioxanone Homopolymers | Poly(1,3-dioxan-2-one) (PDS) | |
| | | Poly(1,4-dioxan-2-one)(PDS) | 107°C |
| | Copolymers of poly(p-dioxanone) | Poly(p-dioxanone-co-L-(-)-lactide) | |
| | | Poly(p-dioxanone-b-glycolide) | |
| | | Poly(p-dioxanone-co-glycolide) | |
| | | Poly(p-dioxanone-co-ε-caprolactone) | |
| | | Poly(p-dioxanone-co-glycolide-co-lactide) | |
| | | Poly(p-dioxanone-co-alkylene oxide) | |
| | | Poly(p-dioxanone-ran-glycolide-ran-lactide) | 150°C ~ 160°C |
| | | Poly(p-dioxanone-b-trimethylene carbonate-b-glycolide) | |

FIGURE 2

| Category and Name | | | Melting point/range | Remarks |
|---|---|---|---|---|
| Polyanhydrides | Aliphatic polyanhydride | Poly(sebacic anhydride)( PSA) | 78°C ~ 82°C | |
| | | Poly(dodecanoic anhydride) (PDA) | 70°C | |
| | | Poly(fumaric anhydride) (PFA) | | |
| | | Poly(adipic anhydride) (PAA) | | |
| | Unsaturated polyanhydride | Poly(crotonylene dianhydride) | | |
| | | Poly(4,4'-stilbendicarboxylic anhydride)(STDA) | | |
| | Aromatic polyanhydride | Poly(terephthalic acid)(PTA) | 400°C | |
| | Poly(aromatic Fatty acid anhydride) | TA-CPP | | Terephthalic acid (TA) |
| | | CPP-IPA | | 1,3-bis(carboxyphenoxy) propane (CPP) |
| | | TA-IPA | | Iso-phthalic acid (IPA) |
| | | TA-SA | | Sebacic acid (SA) |
| | | CPP-SA | | |
| | | IPA-SA | | |
| | Poly(ester anhydride) and poly(aether anhydride) | | | |
| | Fatty Acid based Polyanhrides | | | |
| | Capped polyanhydride | | | |

FIGURE 3

| | | | | |
|---|---|---|---|---|
| | Amino acid based Polyanhydrides | Poly(methylene-bis(*p*-carboxyl benzamide) ) | | |
| | | Poly(trimellitic acid-1,2,4,5-Benzenetetracarboxylic acid) | | |
| | | Poly(trimellitic acid imide dicarboxyl-co-polyimide decanedioci) | | |
| | Branched polyanhydrides | | | |
| | Photo crosslinking polyanhydrides | | | |
| | Mixtures of polyanhydrides | | | |
| Polyphosphazene | Poly(organic phosphazene ) | | | |
| | Poly(dichloropolyphosphazene ) | | | |
| | Polyphosphazene amino acid derivatives and polyphosphazene with amino acid side groups (POP) | Amino-polyphosphazene | | |
| | | Alkoxy-polyphosphazene | | |

FIGURE 3 (continued)

| Category and Name | | | Melting point/range |
|---|---|---|---|
| Poly(ether ester) | Poly(ether ester) I | | |
| | Poly(ether ester) II | | |
| | Poly(ether ester) III | | |
| | poly(ether ester) IV | | |
| Poly(amino acid) | Poly-amino-acids and copolymers | Poly(glutamic acid) | |
| | | Polyaspartate | |
| | | Poly(L-lysine) | |
| | | Poly(leucine-co-benzyl L-glutamate) | |
| | | Poly(L-leucine-co-L-glutamic acid- methyl ester-co-L-glutamic acid) | |
| | | Poly(L-leucine-co-L-aspartic acid) | |
| | Pseudo polyamino acids | Poly(N-acyl-4-hydroxyproline ester ) | |
| | | Poly(N-acyl-L-tryptophan ester) | |
| | | Poly(amino acid-imine carbonate) | |
| | | Poly(amino acid-carbonate) | |
| | Poly(amino acid-co-non-amino acid) | Poly(poly(ethylene glycol)-co-Aspartate) | |
| | | Poly(poly(ethylene glycol)-co-Lysine) | |
| | | Poly(propylene glycol)-co- Poly(glutamic acid) | |
| | | Poly(methyl-siloxane)-co- Poly(Glutamic acid) | |
| | L-Tyrosine-derived polymers | Tyrosine-derived polycarbonate | |
| | | Tyrosine-derived polyaromatic compounds | |
| | | Tyrosine-derived polycarbonate | |
| Polycyanoacrylate | | Poly(butylcyanoacrylate) (PBCA) | 150°C ~ 320°C |
| | | Poly(isobutylcyanoacrylate)(PiBCA) | |
| | | Poly(ethylcyanoacrylate) | 140°C ~ 180°C |
| | | Poly(propylcyanoacrylate) | |
| | | Poly(methylcyanoacrylate) | 140°C ~ 180°C |
| Polyether | | Poly(ethylene glycol) | |
| | | Polyoxyethylene | 65°C ~ 70°C |
| Poloxamer | | | |

FIGURE 4

| Category and Name | | | Melting point/range | Remarks |
|---|---|---|---|---|
| Genetically engineered protein polymers | | | | |
| Conductive, elastic, and plastic protein based polymers | | | | |
| Polyhydroxyalkanoates (PHA) | Polymerhydroxy homopolymers | Poly (β-hydroxybutyrate) (PHB) | 179°C | |
| | | Polyhydroxyvalerate (PHV) | | |
| | Poly(hydroxy alkanates) copolymers | Poly(3-hydroxybutyrate(3HB)-co-4-hydroxyvalerate(4HV)) | 144°C | |
| | | 3HB/4HB copolymer | 159°C | 3HB/4HB=91/9 |
| | | 3HB/3HV copolymer | 91°C | 3HB/3HV =1/1 |
| | | 3HB/4HB copolymer | | |

FIGURE 5

| Category and Name | | Melting point/range |
|---|---|---|
| Higher fatty acid | Stearic acid | ≥54°C |
| | Citric acid monohydrate | around 100°C |
| Higher fatty alcohol | Cholesterol | 147°C~150°C |
| | Stearyl alcohol | 59.4~59.8°C |
| Higher fatty ester | Ethylene glycol palmitostearate | 54°C~65°C |
| | Diethylene glycol palmitostearate | 43°C~50°C |
| | Ethylene glycol palmitate | |
| | Ethylene glycol stearate | 43°C~50°C |
| | Glyceryl behenate | 65°C~77°C |
| | Glyceryl monostearate | 55°C~60°C |
| | Glyceryl palmitostearate | <52°C~55°C |
| | Hydrogenated castor oil | 83°C~88°C |
| | Hydrogenated vegetable oil | 61°C~66°C |
| Waxes | Carnauba wax | 81°C~88°C |
| | Cetyl Esters wax | 43°C~55°C |
| | Microcrystalline wax | 54°C~102°C |
| | Nonionic emulsifying wax | 50°C~54°C |
| | White wax | 62°C~65°C |
| | Yellow wax | 61°C~65°C |

FIGURE 6

| Category and Name | | Melting point/range | Remarks |
|---|---|---|---|
| Ethylenes | Poly(vinyl alcohol)(PVA) | 228°C | Complete alcoholysis |
| | | 180°C ~ 190°C | Partial alcoholysis |
| | Polyvinylpyrrolidone(PVP) | | 150°C Softening |
| | Ethylene vinyl acetate copolymer (EVA) | | |
| Poly(vinyl acetate) | | | |
| Polymethacrylate | | | 126°C Softening |
| Polysiloxanerubber | | | |
| Hydroxyapatite Derivatives | | | |
| Polycarbonate | | | |
| Polyacrylate | | | |
| Polyurethane | | | |
| Carbomer | | | Tg 100°C ~ 105°C |

FIGURE 7

| | Name | Melting point/range |
|---|---|---|
| Cyclodextrins | α-Cyclodextrins | 250°C~260°C |
| | β-Cyclodextrins | 255°C~265°C |
| | γ-Cyclodextrins | 240°C~245°C |
| | 2-hydroxyethyl-β-Cyclodextrins | |
| | 2-hydroxypropyl-β-Cyclodextrins | |
| | 3-hydroxypropyl-β-Cyclodextrins | |
| | Trimethyl-β-Cyclodextrins | |

FIGURE 8

| | Name | MW(1×10$^5$) | Melting point/range |
|---|---|---|---|
| Poly(lactic acid) | Poly(D,L-lactic acid) | 0.5~70 | Amorphous, softening around 120°C |
| | Poly(L-lactic acid) | 1~5 | 162~168°C |
| | | 5~10 | 168~172°C |
| | | 10~30 | 172~178°C |
| | | 30~50 | 178~184°C |
| | | 50~70 | 184~188°C |
| Poly(D,L-lactic-co-glycolic acid) | D,L-lactic acid/Glycolic acid =90/10 | 0.5~30 | |
| | D,L-lactic acid/Glycolic acid =80/20 | 0.5~30 | |
| | D,L-lactic acid/Glycolic acid =75/25 | 0.5~30 | |
| | D,L-lactic acid/Glycolic acid =60/40 | 0.5~20 | |
| | D,L-lactic acid/Glycolic acid =50/50 | 0.5~20 | |
| Poly(L-lactic-co-glycolic acid) Copolymers | L-lactic acid/Glycolic acid =95/5 | 1~5 | 72~82°C |
| | | 5~10 | 82~90°C |
| | | 10~30 | 90~100°C |
| | | 30~50 | 100~108°C |
| | | 50~70 | 108~120°C |
| | L-lactic acid/Glycolic acid =90/10 | 1~5 | 70~79°C |
| | | 5~10 | 79~86°C |
| | | 10~30 | 86~95°C |
| | | 30~50 | 95~103°C |
| | | 50~70 | 103~115°C |
| | L-lactic acid/Glycolic acid =85/15 | 1~5 | 70~78°C |
| | | 5~10 | 78~84°C |
| | | 10~30 | 84~92°C |
| | | 30~50 | 92~100°C |
| | | 50~70 | 100~112°C |
| | L-lactic acid/Glycolic acid =75/25 | 1~5 | 68~76°C |
| | | 5~10 | 76~85°C |
| | | 10~30 | 85~92°C |
| | | 30~50 | 92~98°C |
| | | 50~70 | 98~108°C |
| | L-lactic acid/Glycolic acid =65/35 | 1~5 | 65~73°C |
| | | 5~10 | 73~80°C |
| | | 10~30 | 80~88°C |
| | | 30~50 | 88~95°C |
| | | 50~70 | 95~105°C |
| | L-lactic acid/Glycolic acid =50/50 | 1~5 | 62~70°C |
| | | 5~10 | 70~74°C |
| | | 10~30 | 74~80°C |
| | | 30~50 | 80~86°C |
| | | 30~50 | 86~93°C |

FIGURE 9

| | Name | Melting point/range |
|---|---|---|
| Poly(*p*-dioxanon-co-glycolide) | Poly(*p*-dioxanon-co-glycolide)(20:80) | 210°C |
| | Poly(*p*-dioxanon-co-glycolide)(30:70) | 205°C |
| | Poly(*p*-dioxanon-co-glycolide)(40:60) | 200°C |
| | Poly(*p*-dioxanon-co-glycolide)(50:50) | 200°C |
| | Poly(*p*-dioxanon-co-glycolide)(60:40) | 170°C |

FIGURE 10

| Name | | Melting point/range |
|---|---|---|
| Poly-(CPP-SA) | Poly-SA   100% | 86°C |
| | Poly-(CPP-SA) 4:96 | 76°C |
| | Poly-(CPP-SA) 13:87 | 75°C |
| | Poly-(CPP-SA) 22:78 | 66°C |
| | Poly-(CPP-SA) 31:69 | 66°C |
| | Poly-(CPP-SA) 41:59 | 178°C |
| | Poly-(CPP-SA) 46:54 | 185°C |
| | Poly-(CPP-SA) 60:40 | 200°C |
| | Poly-(CPP-SA) 80:20 | 205°C |

FIGURE 11

| Name | Average Molecular Weight | Melting point/range |
|---|---|---|
| Polyethylene glycol | PEG1000 | 37°C~40°C |
| | PEG1500 | 44°C~48°C |
| | PEG2000 | 45°C~50°C |
| | PEG3000 | 48°C~54°C |
| | PEG4000 | 50°C~58°C |
| | PEG6000 | 55°C~63°C |
| | PEG8000 | 60°C~63°C |
| | PEG20000 | 60°C~63°C |

FIGURE 12

| Name | Grade | Melting point/range |
|---|---|---|
| Poloxamer | Poloxamer124 | 16°C |
| | Poloxamer188 | 52°C~57°C |
| | Poloxamer237 | 49°C |
| | Poloxamer338 | 57°C |
| | Poloxamer407 | 52°C~57°C |

FIGURE 13

CONTROLLED RELEASING COMPOSITION

FIELD OF THE INVENTION

The present disclosure relates generally to novel controlled release composition comprising a matrix and a plurality of microparticles operably linked to the matrix, and methods of making and using the same.

BACKGROUND OF THE INVENTION

Many diseases or conditions require administration of a constant or sustained level of a medicament or biologically active agent to provide the optimal prophylactic or therapeutic effects. This can be accomplished through a multiple dosing regimen or by employing a system that releases the medicament or biologically active agent in a sustained or controlled fashion. The two main advantages of using controlled release pharmaceutical compositions are the ability to maintain an elevated therapeutic level over a prolonged period of time and an increase in patient compliance obtained by reducing the number of doses necessary to achieve the same effect with a rapid-acting formulation.

Attempts to sustain medication levels include, for example, the use of a controlled release composition comprising biodegradable materials, such as polymeric compositions, containing the medicament. Polymeric controlled delivery has significantly improved the success of many drug therapies. In such a delivery system, pharmacokinetics and biodistribution of the active agent depend upon the physiochemical properties and/or degradation properties of the polymer carriers. The use of these polymeric compositions, for example, in the form of microparticles or microspheres, provides sustained release of medicaments.

Nonetheless, a number of issues hinder the applications of microparticle-based controlled release composition. For example, microparticles have a tendency to form aggregates which can significantly affect the properties of the controlled release composition. In addition, a large amount of solvent need to be added to a microparticle-based controlled release composition before its application, generally with a ratio of 80-90%:10-20%, respectively, which can be very problematic in situations, such as, when injecting the microparticle-based controlled release composition into a solid tumor. Furthermore, microparticles could move relatively easily within a tissue after its implantation. This makes it impractical, if not impossible, for the measurement of the drug release rate in tissues near the implantation site. Therefore, there exists a need for an improved microparticle-based controlled release composition.

SUMMARY OF THE INVENTION

Provided herein are controlled release compositions and methods of preparing the same. Methods of use of the controlled release compositions for treating/preventing/diagnosing conditions in humans or animals are also provided.

In one aspect, the present disclosure provides a controlled release composition comprising a plurality of microparticles operably linked to a matrix, wherein:

the plurality of microparticles comprise a first material and a first active agent;
the matrix comprises a second material;
the first material comprises an initial melting temperature $T_H$;
the second material comprises a complete melting temperature $T_L$;

$\Delta T = T_H - T_L$; and $\Delta T > 0$.

In certain embodiments, the first material or the second material is a polymer or a non-polymeric organic compound. In certain embodiments, the first material and the second material are either a polymer or a non-polymeric organic compound. In certain embodiments, the first material is a polymer and the second material is a non-polymeric organic compound. In certain embodiments, the first material is a non-polymeric organic compound and the second material is a polymer. In certain embodiments, the first material comprises a combination of a polymer and a non-polymeric organic compound. In certain embodiments, the second material comprises a combination of a polymer and a non-polymeric organic compound.

In certain embodiments, the first material and/or the second material comprises a polymer formed by at least one monomer independently selected from the group consisting of: L-lactic acid, saccharide, ethylene glycol oxalate, p-dioxanone, ε-caprolactone, ethylcyanoacrylate, butylcyanoacrylate, β-hydroxybutyrate, 3-hydroxybutyrate, 4-hydroxyvalerate, 1,3-bis(carboxyphenoxy)propane, sebacic acid, D-glucose, acetate of glucose, glucose substituted with hydroxyl groups, glycolic acid, ε-caprolacton, 1,4-dioxan-2-one, sebacic anhydride, dodecanoic anhydride, ethylene glycol, oxyethylene, 1,3-bis(carboxyphenoxy)propane, 3-hydroxybutyrate, 3-hydroxyvalerate, caprolactone, methyl methacrylate, gelatin, isoleucine, leucine, alanine, asparagine, lysine, methionine, aspartic acid, cysteine, tryptophan, valine, glycine, proline, serine, tyrosine, arginine, histidine, phenylalanine, glutamic acid, threonine, glutamine, adenine, guanine, thymine, cytosine and dimethyl siloxane.

In certain embodiments, the first material and/or the second material can be independently selected from the group consisting of poly(L-lactic acid), dextran, poly(ethylene glycol oxalate), poly(p-dioxanone-co-ε-caprolactone), poly(ethylcyanoacrylate), poly(butylcyanoacrylate), poly (β-hydroxybutyrate), poly(3-hydroxybutyrate-co-4-hydroxyvalerate), poly(1,3-bis(carboxyphenoxy)propane-co-sebacic acid), cholesterol, cellulose acetate, hydroxypropyl methyl cellulose phthalate, zein, poly(L-lactic-co-glycolic acid), poly(ε-caprolacton), poly(1,4-dioxan-2-one), poly(sebacic anhydride), poly(dodecanoic anhydride), poly(ethylene glycol), polyoxyethylene, stearic acid, stearyl alcohol; ethylene glycol palm itostearate, cetyl esters wax, poly(1,3-bis(carboxyphenoxy)propane-co-sebacic acid), poly(3-hydroxybutyrate-co-3-hydroxyvalerate), Carnauba wax, ethylcellulose, octadecanol, polycaprolactone, poly(methyl methacrylate), poly(gelatin), and silicone rubber.

In certain embodiments, the $\Delta T$ can be $\geq 2°$ C. In certain of these embodiments, the $\Delta T$ can be $\geq 5°$ C., in other embodiments, $\geq 10°$ C., $\geq 20°$ C., $\geq 30°$ C., $\geq 40°$ C., or $\geq 50°$ C.

In certain embodiments, at least one of the first material and the second material is biodegradable. In certain embodiments, the first material is biodegradable. In certain embodiments, the second material is biodegradable. In certain embodiments, the second material degrades faster than the first material.

In certain embodiments, at least one of the plurality of microparticles further comprises a first additive. In certain embodiments, at least one of the plurality of microparticles further comprises a coating.

In certain embodiments, at least one of the plurality of microparticles comprises about 2% to about 98% of the first material, about 2% to about 98% of the first active agent, about 0% to about 30% of the first additive by weight.

In certain embodiments, the matrix further comprises a second active agent. In certain embodiments, the matrix further comprises a second additive.

In certain embodiments, the controlled release composition comprises about 1% to about 95% of the microparticles, about 2% to about 98% of the second material, about 0% to about 70% of the second active agent, and about 0% to about 30% of the second additive by weight.

In certain embodiments, the plurality of microparticles can be uniformly distributed or embedded in the matrix. In certain embodiments, the plurality of microparticles can be distributed or embedded in the matrix in accordance with a pre-determined pattern. In certain embodiments, the plurality of microparticles can be randomly distributed or embedded in the matrix. In certain embodiments, the plurality of microparticles can be coated on the surface of the matrix. In certain embodiments, a portion of the plurality of microparticles can be embedded within the matrix and the rest of the plurality of microparticles can be coated on the surface of the matrix.

In certain embodiments, the controlled release composition further comprises a coating.

In certain embodiments, at least one of the plurality of microparticles can be of a size of about 1 μm to about 5000 μm in diameter. In certain of these embodiments, at least one of the plurality of microparticles can be of a size of about 20 μm to about 1000 μm, in other embodiments, about 50 μm to about 100 or about 120 μm to about 1000 μm.

In certain embodiments, the controlled release composition can be of a size of about 0.2 mm to about 200 mm.

In another aspect, the present disclosure provides a method for making a controlled release composition comprising a plurality of microparticles operably-linked to a matrix, wherein the method comprising:

preparing a plurality of microparticles comprising a first material and a first active agent; and applying the plurality of microparticles to a matrix-forming composition comprising a second material, thereby forming the controlled release composition, wherein:

the first material comprises an initial melting temperature $T_H$;

the second material comprises a complete melting temperature $T_L$;

$$\Delta T = T_H - T_L; \text{ and}$$

$$\Delta T > 0.$$

In certain embodiments, the method further comprises heating the matrix-forming composition to a temperature $T_m$, wherein $T_H > T_m > T_L$. In certain embodiments, $T_H - T_m$ and/or $T_m - T_L$ can be about 5° C., ≥ about 10° C. or ≥ about 20° C. In certain embodiments, the method further comprises providing a coating to the plurality of microparticles and/or the controlled release composition.

In certain embodiments, the method further comprises dissolving the matrix-forming composition in a solvent, wherein the second material is soluble in the solvent while the first material or the microparticles comprising the first material is substantially insoluble in the solvent.

In another aspect, the present disclosure provides a method of treating a condition in a subject comprising administering to the subject the controlled release composition provided herein. In certain embodiments, the condition can be a pathological condition, a physiological condition or a cosmetic condition.

Other features and advantages of the present disclosure will become apparent from the following detailed description. It should be understood, however, that the detailed description and the specific examples, while indicating the preferred embodiments of the present disclosure, are given by way of illustration only, since various changes and modifications within the spirit and scope of the present disclosure will become apparent to those skilled in the art from this detailed description.

BRIEF DESCRIPTION OF THE FIGURES

FIG. 1 shows a representative list of natural and semi-synthetic biodegradable materials suitable for use in making a controlled release composition in accordance with one embodiment of the present disclosure.

FIG. 2 shows a representative list of synthetic biodegradable materials suitable for use in making a controlled release composition in accordance with one embodiment of the present disclosure.

FIG. 3 shows a representative list of synthetic biodegradable materials suitable for use in making a controlled release composition in accordance with one embodiment of the present disclosure.

FIG. 4 shows a representative list of synthetic biodegradable materials suitable for use in making a controlled release composition in accordance with one embodiment of the present disclosure.

FIG. 5 shows a representative list of biodegradable materials suitable for use in making a controlled release composition in accordance with one embodiment of the present disclosure.

FIG. 6 shows a representative list of organic compounds suitable for use in making a controlled release composition in accordance with one embodiment of the present disclosure.

FIG. 7 shows a representative list of non-biodegradable materials suitable for use in making a controlled release composition in accordance with one embodiment of the present disclosure.

FIG. 8 shows a representative list of cyclodextrin materials suitable for use in making a controlled release composition in accordance with one embodiment of the present disclosure.

FIG. 9 shows a representative list of materials suitable for use in making a controlled release composition in accordance with one embodiment of the present disclosure.

FIG. 10 shows a representative list of poly(p-dioxanon-co-glycolide) polymers suitable for use in making a controlled release composition in accordance with one embodiment of the present disclosure.

FIG. 11 shows a representative list of poly-(CPP-SA) polymers suitable for use in making a controlled release composition in accordance with one embodiment of the present disclosure.

FIG. 12 shows a representative list of polyethylene glycol polymers suitable for use in making a controlled release composition in accordance with one embodiment of the present disclosure.

FIG. 13 shows a representative list of poloxamer polymers suitable for use in making a controlled release composition in accordance with one embodiment of the present disclosure.

DETAILED DESCRIPTION OF THE INVENTION

I. Controlled Release Composition

Figure 14:
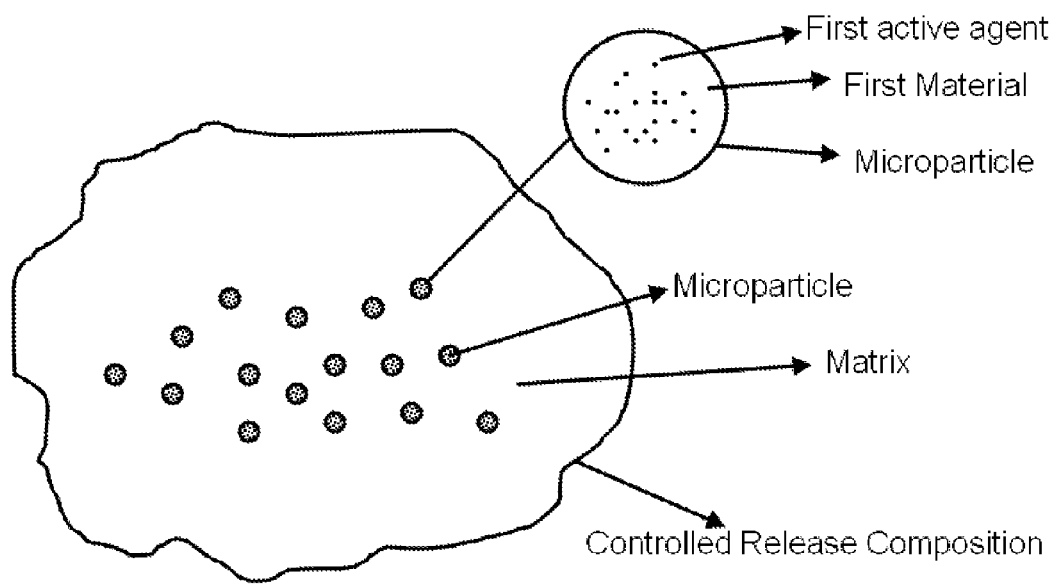
FIG. 14 shows two schematic drawings illustrating the constitution of a controlled release composition.
Figure 14:
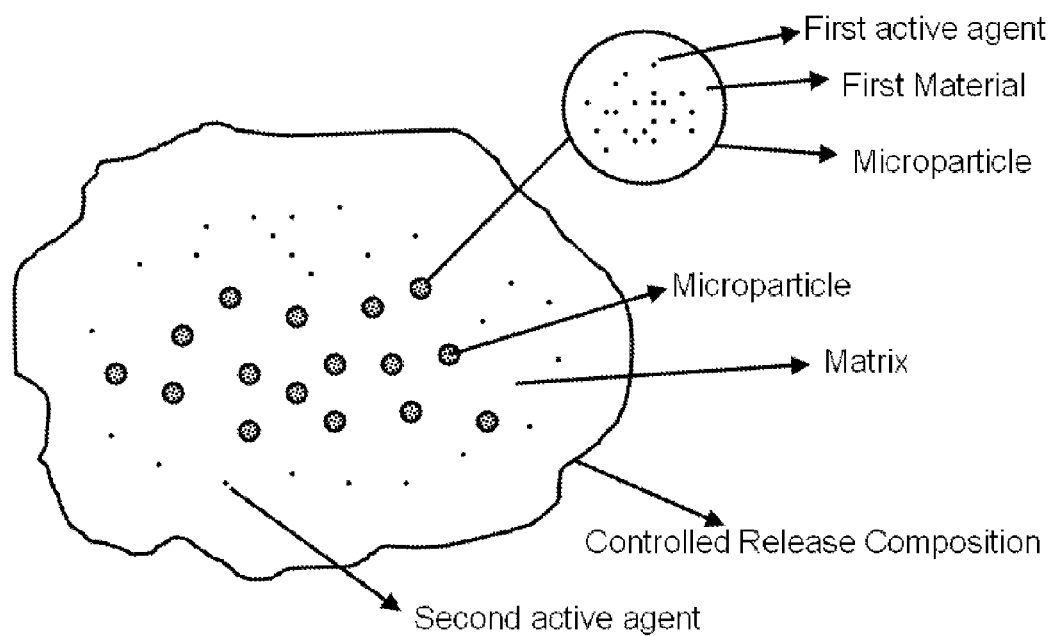

The controlled release compositions provided herein comprise a plurality of microparticles operably linked to a matrix, wherein the plurality of microparticles comprise a first material; the matrix comprises a second material; and the melting temperature of the first material is higher than the melting temperature of the second material.

In one aspect, the present disclosure provides a controlled release composition comprising a plurality of microparticles operably linked to a matrix, wherein the plurality of microparticles comprise a first material and a first active agent, and the matrix comprises a second material; the first material comprises an initial melting temperature $T_H$; the second material comprises a complete melting temperature $T_L$; $\Delta T=T_H-T_L$; and $\Delta T>0$.

A. Materials

The controlled release composition comprises a first material, a second material and a first active agent. The first material and/or the second material can be any suitable material known in the art. The term "material" as used herein includes polymers, non-polymeric organic compounds, and a combination thereof. In certain embodiments, the first material or the second material is a polymer or a non-polymeric organic compound.

In certain embodiments, the first material comprises a polymer. In certain embodiments, the second material comprises a polymer. Polymers include: 1) polymeric molecules comprising two or more repeating units bonded by covalent linkages, and 2) polymeric molecules formed from small molecules by polymerization reaction. The repeating units of polymers can be any chemical compounds that are suitable for forming a chemical union. The repeating units are also called monomer. Illustrative examples of monomers include alkanes, alkenes, alkynes, acids, alcohols, esters, amines, amides, ketones, ethers, anhydrides, nitrides, nucleotide, nucleic acid, amino acid, and saccharide. In certain embodiments, a monomer itself can be a polymer. For example, gelatin, which comprises repeating units of amino acids, is itself a polymer (protein), but gelatin can be further crosslinked to form a poly(gelatin) comprising covalently linked aggregation of gelatin.

The first material and/or the second material in the present disclosure can comprise a polymer formed by suitable monomers known in the art. In certain embodiments, the monomer is independently selected from the group consisting of: L-lactic acid, saccharide, ethylene glycol oxalate, p-dioxanone, ε-caprolactone, ethylcyanoacrylate, butylcyanoacrylate, β-hydroxybutyrate, 3-hydroxybutyrate, 4-hydroxyvalerate, 1,3-bis(carboxyphenoxy)propane, sebacic acid, D-glucose, acetate of glucose, glucose substituted with hydroxyl groups, glycolic acid, ε-caprolacton, 1,4-dioxan-2-one, sebacic anhydride, dodecanoic anhydride, ethylene glycol, oxyethylene, 1,3-bis(carboxyphenoxy)propane, 3-hydroxyvalerate, caprolactone, methyl methacrylate, gelatin, amino acid such as isoleucine, leucine, alanine, asparagine, lysine, methionine, aspartic acid, cysteine, tryptophan, valine, glycine, proline, serine, tyrosine, arginine, histidine, phenylalanine, glutamic acid, threonine, and glutamine, nucleotide such as adenine, guanine, thymine, cytosine and dimethyl siloxane.

The first material and/or the second material in the present disclosure can comprise any suitable polymers known in the art. In certain embodiments, the first material and/or the second material can be natural polymers, semi-synthetic polymers, synthetic polymers, or a combination thereof. Natural polymers include polysaccharides (such as starch, cellulose and gums), polypeptides, proteins, and polynucleotides. Illustrative examples of natural polymers are, starch, dextrin, microcrystalline cellulose, acacia, chitosan, hyaluronic acid, alginate, dextran, tragacanth gum, xanthan gum, zein, collagen, gelatin, and shellac. More examples of natural polymers are provided in FIG. 1. Semi-synthetic polymers include a chemically modified naturally occurring polymer. Illustrative examples of semi-synthetic polymers are cross-linked starch, carboxymethyl cellulose, hydroxypropyl methyl cellulose phthalate, and deacetylated-chitosan. More examples of semi-synthetic polymers are provided in FIG. 1. Synthetic polymers can be any polymers formed by artificial polymerization of monomers. Examples of synthetic polymers are, polyoxyethylene, poly(L-lactic-co-glycolic acid), poly(lactic acid), and poly(p-dioxanon-co-glycolide). More examples of semi-synthetic polymers are provided in FIGS. 2-5.

In certain embodiments, the first material and/or the second material comprise a polymer formed by the same repeating units or monomer (homopolymers). For example, poly(ethylene glycol) comprises repeating units of ethylene glycol. Homopolymers comprising the same monomer can have various weight average molecular weight due to their different polymerization degrees, and consequently, may have various melting temperatures. For example, poly(ethylene glycol)s (PEGs) have a weight average molecular weight varying in a wide range such as PEG1000, PEG1500, PEG2000, PEG6000, and PEG20000.

In certain embodiments, the first material and/or the second material comprise a polymer formed by at least two different repeating units or monomer (heteropolymer). For example, poly(L-lactic-co-glycolic acid) comprises repeating units of both L-lactic acid and glycolic acid. Heteropolymer comprising the same monomers can have various mole fraction ratios of the monomers, and consequently, may have various melting temperatures. For example, poly(L-lactic-co-glycolic acid) has a varied mole fraction ratio of L-lactic acid to glycolic acid of 90:10, 80:20, 75:25, 60:40, or 50:50.

In certain embodiments, the first material and/of the second material can be selected from any polymer listed in FIGS. 1-5 and FIGS. 7-13.

In certain embodiments, the first material comprises a non-polymeric organic compound. In certain embodiments, the second material comprises a non-polymeric organic compound. The non-polymeric organic compounds include any organic compounds that do not comprise repeating units. Illustrative examples of non-polymeric organic compounds include, fatty acids (such as stearic acid, citric acid), fatty alcohols (such as cholesterol, stearyl alcohol), fatty esters (such as ethylene glycol palm itosterate, diethylene glycol palm itosterate, and glyceryl behenate), waxes (such as Carnauba wax, microcrystalline wax, and white wax), and any suitable combinations. In certain embodiments, a non-polymeric compound can be a mixture comprising more than one organic compound. For example, Carnauba wax comprises a combination of about 80-85% of ester of fatty acids, 10-16% of fatty alcohols, 3-6% of acids, and 1-3% of hydrocarbons.

In certain embodiments, the first material and/or the second material can be selected from any non-polymeric organic compounds listed in FIG. 6.

In certain embodiments, the first material comprises a polymer and the second material comprises a non-polymeric organic compound, or vice versa.

In certain embodiments, the first material comprises a combination of a polymer and a non-polymeric organic compound. In certain embodiments, the second material comprises a combination of a polymer and a non-polymeric organic compound.

The first material and/or the second material can be biodegradable materials, non-biodegradable materials, or a combination thereof. The term "biodegradable material" refers to a material that is capable of being completely or substantially degraded, eroded or absorbed when exposed to either an in vivo environment or an in vitro environment having physical, chemical, or biological characteristics substantially similar to those of the in vivo environment within a living organism. A material is capable of being degraded or eroded when it can be gradually broken-down, resorbed, absorbed and/or eliminated by, for example, hydrolysis, enzymolysis, oxidation, metabolic processes, bulk or surface erosion, and the like within a living organism. The term "living organism" as used herein refers to human and animals. The biodegradable material degrades into non-toxic components in a living organism, and its degradation may not cause substantial tissue irritation or necrosis at the target tissue site. Illustrative examples of biodegradable materials include, starch, zein, poly(lactic acid), poly(1,3-dioxan-2-one), poly(sebacic anhydride), alkoxy-polyphosphazene, poly(ether ester), poly(glutamic acid), poloxamer, cholesterol, stearic acid, and stearic alcohol. More examples of biodegradable materials are provided in FIGS. 1-5. The non-biodegradable materials are material that cannot be degraded in a living organism. Illustrative examples of non-biodegradable materials include poly(vinyl alcohol), poly(vinyl acetate), polyurethane, and Carbomer. More examples of non-biodegradable materials are provided in FIG. 7.

In certain embodiments, the first material and/or the second material can be independently selected from the group consisting of: poly(L-lactic acid), dextran, poly(ethylene glycol oxalate), poly(p-dioxanone-co-$\epsilon$-caprolactone), poly(ethylcyanoacrylate), poly(butylcyanoacrylate), poly($\mu$-hydroxybutyrate), poly(3-hydroxybutyrate-co-4-hydroxyvalerate), poly(1,3-bis(carboxyphenoxy)propane-co-sebacic acid), cholesterol, cellulose acetate, hydroxypropyl methyl cellulose phthalate, zein, poly(L-lactic-co-glycolic acid), poly($\epsilon$-caprolacton), poly(1,4-dioxan-2-one), poly(sebacic anhydride), poly(dodecanoic anhydride), poly(ethylene glycol), polyoxyethylene, stearic acid, stearyl alcohol; ethylene glycol palm itostearate, cetyl esters wax, poly(1,3-bis(carboxyphenoxy)propane-co-sebacic acid), and poly(3-hydroxybutyrate-co-4-hydroxyvalerate), Carnauba wax, ethylcellulose, octadecanol, polycaprolactone, poly(methyl methacrylate), poly(gelatin), and silicone rubber.

In certain embodiments, the first material comprises a combination of more than one material. In certain embodiments, the first material comprises at least one of: (i) a combination of poly(L-lactic acid) and at least one compound selected from the group consisting of: dextran, poly(ethylene glycol oxalate), poly(p-dioxanone-co-$\epsilon$-caprolactone), poly(ethylcyanoacrylate), poly(butylcyanoacrylate), poly ($\beta$-hydroxybutyrate), poly(3-hydroxybutyrate-co-4-hydroxyvalerate), poly(1,3-bis(carboxyphenoxy)propane-co-sebacic acid), cholesterol, cellulose acetate, hydroxypropyl methyl cellulose phthalate, and zein; (ii) a combination of poly(ethylene glycol oxalate) and at least one compound selected from the group consisting of: dextran, poly(p-dioxanone-co-$\epsilon$-caprolactone), poly(ethylcyanoacrylate), poly(butylcyanoacrylate), poly (($\beta$-hydroxybutyrate), poly (3-hydroxybutyrate-co-4-hydroxyvalerate), poly(1,3-bis(carboxyphenoxy)propane-co-sebacic acid), cholesterol, cellulose acetate, hydroxypropyl methyl cellulose phthalate, and zein; (iii) a combination of poly($\beta$-hydroxybutyrate) and at least one compound selected from the group consisting of: dextran, poly(p-dioxanone-co-$\epsilon$-caprolactone), poly(ethylcyanoacrylate), poly(butylcyanoacrylate), poly(3-hydroxybutyrate-co-4-hydroxyvalerate), poly(1,3-bis(carboxyphenoxy)propane-co-sebacic acid), cholesterol, cellulose acetate, hydroxypropyl methyl cellulose phthalate, and zein; (iv) a combination of poly(1,3-bis(carboxyphenoxy)propane-co-sebacic acid) and at least one compound selected from the group consisting of: dextran, poly(p-dioxanone-co-$\epsilon$-caprolactone), poly(ethylcyanoacrylate), poly(3-hydroxybutyrate-co-4-hydroxyvalerate), cholesterol, cellulose acetate, hydroxypropyl methyl cellulose phthalate, and zein; and (v) a combination of poly(butylcyanoacrylate) and at least one compound selected from the group consisting of: dextran, poly(p-dioxanone-co-$\epsilon$-caprolactone), poly(ethylcyanoacrylate), poly(3-hydroxybutyrate-co-4-hydroxyvalerate), poly(1,3-bis(carboxyphenoxy)propane-co-sebacic acid), cholesterol, cellulose acetate, hydroxypropyl methyl cellulose phthalate, and zein.

In certain embodiments, the second material comprises a combination of more than one material. In certain embodiments, the second material comprise at least one of: (i) a combination of poly(L-lactic-co-glycolic acid) and at least one compound selected from the group consisting of: poly($\epsilon$-caprolacton), poly(1,4-dioxan-2-one), poly(sebacic anhydride), poly(dodecanoic anhydride), poly(ethylene glycol), polyoxyethylene, stearic acid, stearyl alcohol; ethylene glycol palm itostearate, cetyl esters wax, poly(1,3-bis(carboxyphenoxy)propane-co-sebacic acid), and poly(3-hydroxybutyrate-co-3-hydroxyvalerate); (ii) a combination of poly($\epsilon$-caprolacton) and at least one compound selected from the group consisting of: poly(1,4-dioxan-2-one), poly(sebacic anhydride), poly(dodecanoic anhydride), poly(ethylene glycol), polyoxyethylene, stearic acid, stearyl alcohol; ethylene glycol palmitostearate, cetyl esters wax, poly(1,3-bis(carboxyphenoxy)propane-co-sebacic acid), and poly(3-hydroxybutyrate-co-3-hydroxyvalerate); (iii) a combination of poly(1,4-dioxan-2-one) and at least one compound selected from the group consisting of: poly(sebacic anhydride), poly(dodecanoic anhydride), poly(ethylene glycol), polyoxyethylene, stearic acid, stearyl alcohol; ethylene glycol palmitostearate, cetyl esters wax, poly(1,3-bis(carboxyphenoxy)propane-co-sebacic acid), and poly(3-hydroxybutyrate-co-3-hydroxyvalerate); and (iv) a combination of poly(sebacic anhydride) and at least one compound selected from the group consisting of: poly(dodecanoic anhydride), poly(ethylene glycol), polyoxyethylene, stearic acid, stearyl alcohol; ethylene glycol palmitostearate, cetyl esters wax, poly(1,3-bis(carboxyphenoxy)propane-co-sebacic acid), and poly(3-hydroxybutyrate-co-3-hydroxyvalerate).

In certain embodiments, the microparticle or the matrix comprises a homogenous material, or a heterogeneous material. The homogeneous material is a material comprising the same polymer, the same repeating units, or the same non-polymeric organic compound. The heterogeneous material is a material comprising different polymers, different monomers, different non-polymeric organic compounds, or a combination thereof.

B. Melting Temperature

The first material and the second material can be selected according to their melting temperatures. The term "melting temperature" can be construed broadly in the present disclosure to include the following temperatures: 1) melting temperature at which the solid form of the material is in equilibrium with the liquid form of the material; 2) softening temperature at which the solid material softens; and 3) decomposition temperature at which the chemical structure of the material changes. It is well known in the art that when under heat exposure, solid materials melt and transform into its liquid form, or soften and decompose without generating any liquid form of the material, or decompose without softening or melting. Melting generally takes place over a temperature range at which the solid is in equilibrium with its liquid, and as the temperature rises, the solid eventually changes to its liquid. Some materials do not melt but softens over a temperature range. Softening temperature is generally determined by slowly heating the testing material under a constant load until it experiences a certain deformation. Decomposition takes place above a certain temperature where the chemical structure of the material changes (for example, breaks down or gets oxidized).

Melting temperature of a polymer can be related to its molecular weight and its monomer composition. In certain embodiments, homopolymers having different molecular weights have different melting temperatures. For example, poly(ethylene glycol)s having molecular weights of $10^3$, $1.5 \times 10^3$, $2 \times 10^3$ and $3 \times 10^3$ have melting temperatures of 37-40° C., 44-48° C., 45-50° C., and 48-54° C., respectively. More examples are provided in FIGS. 8, 9, 12, and 13. In certain embodiments, heteropolymers having different mole fraction ratios of the monomers have different melting temperatures. For example, poly(1,3-bis(carboxyphenoxy) propane-co-sebacic acid)s with a mole fraction ratio of 1,3-bis(carboxyphenoxy)propane to sebacic acid of 4:96, 22:78, 41:59, and 60:40 have melting temperatures of 76° C., 66° C., 178° C., and 200° C., respectively. More examples are provided in FIGS. 9-11.

The first material and the second material can be selected according to their initial melting temperatures (Ti) and their complete melting temperatures (Tc). The term "initial melting temperature (Ti)" refers to the temperature at which 1) the material sample first begins to liquefy if the material melts, or 2) the material sample first begins to soften if the material softens but does not melt, or 3) the material sample first begins to decompose if the material does not soften or melt. The term "complete melting temperature (Tc)" refers to the temperature at which 1) the entire material sample becomes liquid if the material melts, or 2) the material sample first begins to decompose if the material does not melt.

In certain embodiments, the material is homogeneous, then Ti and Tc of the material is the Ti and Tc of the homogeneous material. In certain embodiments, the material is heterogeneous, and the Ti of the material is the Ti of the material component having the lowest Ti, and the Tc of the material is the Tc of the material component having the highest Tc. In certain embodiments, the material is heterogeneous and the material is a eutectic mixture, and the Ti of the material is the Ti of the eutectic melting temperature, and Tc of the material is the Tc of the eutectic melting temperature. "Eutectic mixture" refers to a heterogeneous material comprising more than one material components at such proportions that all the material components liquefy simultaneously at a temperature which is lower than the melting temperature of any individual component.

Ti and Tc can be determined using methods known in the art, for example, without limitation, differential scanning calorimetry (for review, please refer to: D. Braun et al, Polymer synthesis: theory and practice: fundamentals, methods, experiments, Published by Springer, 2005, Edition 4, p 124-126; R. Koningsveld et al, Polymer phase diagrams: a textbook, Published by Oxford University Press, 2001, p 24), capillary tube based methods (see, for example, R. P. Brown et al, Handbook of polymer testing: physical methods, Published by CRC Press, 1999, p 348-349) or microscope-based methods (see, for example, A. K. Kolb et al, Automatic microscopic method for determination of melting point, Anal. Chem., 1967, 39(10): 1206-1208), Kofler hotblock based method, Vicat test, method of Martens, and heat distortion temperature measurement methods (see, for example, D. Braun et al, Polymer synthesis: theory and practice: fundamentals, methods, experiments, Published by Springer, 2001, Edition 3, p 86-88), decomposition vessel based methods, gas chromatography, thermogravimetric analysis (TGA), or TGA combined with mass spectrometry or TGA combined with FTIR spectroscopy (see, for example, D. Braun et al, Polymer synthesis: theory and practice: fundamentals, methods, experiments, Published by Springer, 2001, Edition 3, p 93-94; D. Braun et al, Polymer synthesis: theory and practice: fundamentals, methods, experiments, Published by Springer, 2005, Edition 4, p 123-124).

The first material and the second material can be selected by the difference in melting temperatures. In certain embodiments, ΔT is calculated by the following equation:

$$\Delta T = T_H - T_L;$$

wherein $T_H$ is the Ti of the first material, and $T_L$ is the Tc of the second material.

In certain embodiments, the first material and the second material can be selected so that their ΔT is >0° C. In certain embodiments, ΔT of the first material and the second material is ≥2° C. In certain embodiments, ΔT of the first material and the second material is ≥5° C. In certain embodiments, ΔT of the first material and the second material is ≥10° C. In certain embodiments, ΔT of the first material and the second material is ≥20° C. In certain embodiments, ΔT of the first material and the second material is ≥30° C. In certain embodiments, ΔT of the first material and the second material is ≥40° C. In certain embodiments, ΔT of the first material and the second material is ≥50° C. Illustrative examples of pairs of the first material and the second material and their respective ΔT are shown in Table 1.

TABLE 1

Illustrative examples of the first material and the second material and their ΔT

| First material | Ti (° C.) | Second material | Tc (° C.) | ΔT (° C.) |
|---|---|---|---|---|
| Carnauba wax | 81 | poly(lactide-co-glycolide acid) (lactide acid/glycolide acid = 90/10) | 79 | 2 |
| Carnauba wax | 81 | poly(lactide-co-glycolide acid) (lactide acid/glycolide acid = 75/25) and stearic alcohol | 76 | 5 |
| Carnauba wax | 81 | polycaprolactone | 62 | 19 |
| Poly(lactide acid) ($M_w = 2 \times 10^4$) | 162 | poly(lactide-co-glycolide acid) (lactide acid/glycolide acid = 75/25, $M_w = 1.6 \times 10^4$) | 76 | 86 |

In certain embodiments, the first material and the second material can be a pair of materials selected from the group consisting of: poly(L-lactic acid) and poly(L-lactic-co-glycolic acid); poly(L-lactic acid) and poly(ε-caprolacton); poly(L-lactic acid) and poly(1,4-dioxan-2-one); poly(L-lactic acid) and poly(sebacic anhydride); poly(L-lactic acid) and poly(dodecanoic anhydride); poly(L-lactic acid) and poly(1,3-bis(carboxyphenoxy)propane-co-sebacic acid);

poly(1,3-bis(carboxyphenoxy)propane-co-sebacic acid) and poly(L-lactic-co-glycolic acid); poly(1,3-bis(carboxyphenoxy)propane-co-sebacic acid) and poly(ε-caprolacton); poly(1,3-bis(carboxyphenoxy)propane-co-sebacic acid) and poly(1,4-dioxan-2-one); poly(butylcyanoacrylate) and poly (L-lactic-co-glycolic acid); poly(butylcyanoacrylate) and poly(1,3-bis(carboxyphenoxy)propane-co-sebacic acid); poly(ethylcyanoacrylate) and poly(L-lactic-co-glycolic acid); poly(ethylcyanoacrylate) and poly(1,3-bis(carboxyphenoxy)propane-co-sebacic acid); poly(ethylene glycol oxalate) and poly(L-lactic-co-glycolic acid); poly(ethylene glycol oxalate) and poly(ε-caprolacton); poly(ethylene glycol oxalate) and poly(1,4-dioxan-2-one); poly(ethylene glycol oxalate) and poly(sebacic anhydride); poly(ethylene glycol oxalate) and poly(dodecanoic anhydride); poly(ethylene glycol oxalate) and poly(1,3-bis(carboxyphenoxy)propane-co-sebacic acid); dextran and poly(butylcyanoacrylate); dextran and poly(ethylcyanoacrylate); dextran and poly(L-lactic acid); dextran and poly(L-lactic-co-glycolic acid); dextran and poly(1,3-bis(carboxyphenoxy)propane-co-sebacic acid); dextran and poly(sebacic anhydride); cellulose acetate and poly(L-lactic acid); cellulose acetate and poly(butylcyanoacrylate); cellulose acetate and poly(L-lactic-co-glycolic acid); cellulose acetate and poly(sebacic anhydride); cellulose acetate and poly(dodecanoic anhydride); Carnauba wax and poly(lactide-co-glycolide); ethylcellulose and octadecanol; Carnauba wax and polycaprolactone; poly(methyl methacrylate) and poly(L-lactide); poly(lactide-co-glycolide) and poly(gelatin); silicone rubber and poly(L-lactide); ethylcellulose and a combination of poly (L-lactic-co-glycolic acid) and poly(ethylene glycol); a combination of poly(L-lactic acid) and dextran and a combination of poly(L-lactic-co-glycolic acid) and poly(ethylene glycol); and dextran and a combination of poly(L-lactide) and poly(L-lactic-co-glycolic acid).

In certain embodiments, the first material and/or the second material can be further selected by their biodegradation rate. In certain embodiments, the first material and/or the second material can be further selected so that the second material degrades faster than the first material.

In certain embodiments, the biodegradation rate of the first material and/or the second material can be determined by measuring the rate of weight loss of the material in a living organism. For example, the rate of weight loss can be measured by a method comprising: preparing an implant with the testing material, implanting a certain amount of such material implant in a living organism, and measuring the weight of the implanted material after a specified time period.

In certain embodiments, the biodegradation rate of the first material and/or the second material can be determined by measuring the rate of intrinsic viscosity loss of the material in a living organism. Without being bound to theory, it is believed that the intrinsic viscosity is be directly related to the molecular weight of a material, in particular, a polymer. The rate of intrinsic viscosity loss of the material can be measured by a method comprising: preparing an implant with the testing material, implanting a certain amount of such material implant in a living organism, sampling a certain amount of the implant after a specified time period and measuring the viscosity of both the implanted sample and the sample before implantation. The viscosity of the sample can be measured using any suitable method known in the art, for example using a glass viscometer such as Ostwald type viscometer and Ubbelohde type viscometer (for review, please refer to: M. Chanda, Introduction to polymer science and chemistry: a problem solving approach, published by CRC Press, 2006, p 218-221).

In certain embodiments, the first material and the second material can be further selected so that the second material degrades faster than the first material, wherein the first material is poly (L-lactide acid) and the second material can be poly(lactide-co-glycolide acid).

C. Active Agent

The controlled release composition of the present disclosure can be a pharmaceutical composition or a cosmetic composition. In certain embodiments, the controlled release composition can be an implantable pharmaceutical composition, such as, without limitation, a medical implant for treating cancer.

The controlled release composition of the present disclosure comprises at least one active agent. In certain embodiments, the microparticles of the controlled release composition comprises a first active agent. In certain embodiments, the matrix of the controlled release composition further comprises a second active agent. In certain embodiments, the first active agent and/or the second active agent comprise one active agent. In certain embodiments, the first active agent and/or the second active agent comprise a combination of at least two active agents. In certain embodiments, the first active agent and the second active agent are the either the same or different. The term "active agent," as used herein, includes without limitation, pharmaceutically active agent, cosmetically active agent, physiologically active agent, or combinations thereof. Exemplary active agents include, without limitation, drugs, medicines, medicaments, medications, remedies, biologicals, chemical entities, new chemical entities, vaccines, herbal extracts, small molecule compounds, nucleic acids, polypeptides, antibodies or functional fragment thereof, polysaccharides, lipids, and combinations thereof. Any active agent suitable for the purposes of the present disclosure known in the art can be used as the first active agent and/or the second active agent.

Illustrative examples of pharmaceutically active agent include, without limitation, local anesthetics, antiepileptic drugs and anticonvulsants, anti-alzheimer's disease drugs, analgesics, antipodagric, anti-hypertensive drugs, antiarrhythmic drugs, diuretic drugs, drugs for treating liver diseases, drugs for treating pancreatic diseases, antihistamine drugs, anti-allergic drugs, glucocorticoid drugs, sex hormone drugs and contraceptive drugs, hypoglycemic drugs, anti-osteoporosis drugs, antibiotics, sulfonamides, quinolones, and other synthetic antibacterial drugs, antituberculous drugs, antiviral drugs, anti-neoplasm drugs, and immunomodulators. Exemplary active agents are listed in Table 2 in detail. Illustrative examples of cosmetically active agents are also listed in Table 2.

TABLE 2

| Class of active agents | Exemplary active agents |
|---|---|
| Local anesthetics | procaine hydrochloride, ropivacaine, oxybuprocaine hydrochloride, tetracaine hydrochloride, mepivacaine hydrochloride, benzocaine, cinchocaine hydrochloride, proxymetacaine, chloroprocaine hydrochloride, etidocaine |

TABLE 2-continued

| Class of active agents | Exemplary active agents |
| --- | --- |
| | hydrochloride, dyclonine hydrochloride, lidocaine hydrochloride, prilocaine hydrochloride, bupivacaine hydrochloride |
| Antiepileptic drugs and anticonvulsants | clonazepam, valproate sodium, halogabide |
| Anti-alzheimer's disease drugs | huperzine a, rivastigmine, dihydroergotoxine mesilate, nicergolin |
| Analgesics | morphine, dihydroetorphine hydrochloride, hydromorphone, sufentanil citrate, alfentanil, remifentanil, buprenorphine hydrochloride, naloxone, nalmefene |
| Antipodagric drugs | colchicine |
| Anti-hypertensive drugs | nifedipine, niludipine, verapamil, nitrendipine, nimodipine, diltiazem, lacidipine, nilvadipine, azelnidipine, amlodipine, felodipine, benidipine, nicardipine, isradipine, bepridil, nisoldipine, manidipine, nicorandil |
| Antiarrhythmic drugs | flestolol, verapamil hydrochloride |
| Diuretic drugs | cyclothiazide, methyclothiazide |
| Drugs for treating liver diseases | cucurbitacin, bifendate, sophora tonkinensis |
| Drugs for treating pancreatic diseases | octreotide |
| Antihistamine drugs | chlorphenamine maleate, dimethindene maleate, clemastine fumarate |
| Anti-allergic drugs | ketotifen, azatadine maleate, levocabastine |
| Glucocorticoid drugs | medrysone, amcinonide, prednisone, clocortolone trimethylacetic acid, triamcinolone acetonide, dexamethasone, mometasone, paramethasone, prednicarbate, budesonide, rimexolone, cloprednol, flunisolide, fludrocortisone, fluticasone |
| Sex hormone drugs and contraceptive drugs | diethylstilbestrol, nilestriol, epimestrol, estradiol, conjugated estrogens, piperazine estrone, estradiol benzoate, chlorotrianisene, hydroxyestrone, estradiol valerate, mestranol, estrone, depo-estradiol, promestriene, dienestrol, estriol, fosfestrol sodium, quinestradol, ethinylestradiol, cyclofenil, prasterone, quinestrol, progesterone, ethisterone, hydroxyprogesterone, medroxyprogesterone, dydrogesterone, megestrol, chlormadinone, norethisterone, demegestone, medrogestone, noretynodrel, dienogest, nomegestrol, norgestrel, drospirenone, norgestimate, desogestrel, ethynodiol diacetate, norgestrienone, quingestanol, gestodene, promegestone, gestrinone, testosterone, danazol, metandienone, gonadorelin, goserelin |
| Hypoglycemic drugs | repaglinide, glibenclamide, voglibose, glimepiride |
| Anti-osteoporosis drugs | teriparatide |
| Antibiotics | benzylpenicillin, procaine benzylpenicillin, benzathine benzylpenicillin, benzylpenicillin v, phenoxymethylpenicillin hydrabamine, methicillin sodium, talampicillin, bacampicillin hydrochloride, lenampicillin hydrochloride, epicillin, ciclacillin, carbenicillin sodium, carfecillin sodium, carindacillin sodium, oxacillin sodium, nafcillin sodium, cloxacillin sodium, dicloxacillin sodium, flucloxacillin sodium, ampicillin, ticarcillin sodium, azlocillin sodium, mezlocillin sodium, piperacillin sodium, tazocillin, sulbenicillin sodium, mecillinam, sultamicillin, ampicloxacillin, amoxicillin, pivampicillin hydrochloride, hetacillin, metampicillin, pivmecillinam hydrochloride, apalcillin sodium, aspoxicillin, temocillin sodium, azidocillin, phenethicillin potassium, propicillin potassium, furbucillin, cefalotin sodium, cefaloridne, cefalexin, cefazolin sodium, cefradine, cefacetrile, cefroxadine, cefapirin sodium, ceftezole, cefathiamidine, cefadroxil, cefuroxime sodium, cefuroxime axetil, cefaclor, cefotiam hydrochloride, cefamandole, ceforanide, cefonicid sodium, cefprozil, cefminox sodium, cefoxitin sodium, cefmetazole sodium, cefotaxime sodium, cefoperazone sodium, sulperazon, ceftazidime, cefclidin, cefsulodin sodium, ceftriaxone sodium, ceftizoxime sodium, latamoxef disodium, flomoxef sodium, cefpimizole sodium, cefpirome, cefepime, cefuzonam, cefmenoxime, cefoselis sulfate, cefbuperazone sodium, cefcapene pivoxil, cefpiramide sodium, cefotetan disodium, cefodizime, ceftibuten, cefixime, cefetamet pivoxil, cefpodoxime proxetil, cefteram pivoxil, cefditoren pivoxil, cefdinir, imipenem, panipenem, meropenem, biapenem, faropenem, aztreonam, carumonam sodium, streptomycin sulfate, neomycin sulfate, paromomycin, lividomycin, astromicin sulfate, micronomicin sulfate, |

TABLE 2-continued

| Class of active agents | Exemplary active agents |
|---|---|
| | gentamicin sulfate, sisomicin sulfate, netilmicin sulfate, dibekacin sulfate, arbekacin sulfate, isepamicin, amikacin sulfate, kanamycin sulfate, tobramycin sulfate, ribostamycin sulfate, etimicin sulfate, spectinomycin, tetracycline hydrochloride, oxytetracycline hydrochloride, doxycycline hydrochloride, minocycline hydrochloride, metacycline hydrochloride, demeclocycline hydrochloride, guamecycline, chloramphenicol, chloramphenicol palmitate, chloramphenicol succinate, thiamphenicol, erythromycin, erythromycin lactobionate, erythromycin estolate, erythromycin ethylsuccinate, roxithromycin, midecamycin, midecamycin acetate, kitasamycin, kitasamycin tartrate, acetylkitasamycin, spiramycin, acetylspiramycin, azithromycin, clarithromycin, rokitamycin, josamycin, rosaramicin, dirithromycin, flutithromycin, telithromycin, lincomycin hydrochloride, clindamycin hydrochloride, clindamycin phosphate, vancomycin hydrochloride, norvancomycin, teicoplanin, polymyxin sulfate, polymyxin e sulfate, colistimethate sodium, bacitracin, fosfomycin, fosfomycin trometamol, novobiocin sodium, linezolid, rifaximin, fusidate sodium |
| Sulfonamides, quinolones, and other synthetic antibacterial drugs | sulfadiazine, sulfamethoxazole, trimethoprim, sulfafurazole, sulfadimidine, sulfamonomethoxine, sulfadoxine, sulfasalazine, sulfacetamide sodium, sulfadiazine silver, nalidixic acid, pefloxacin, enoxacin, ofloxacin, ciprofloxacin, lomefloxacin, pipemidic acid, fleroxacin, grepafloxacin, gemifloxacin, rufloxacin, moxifloxacin, norfloxacin, pazufloxacin, trovafloxacin, sparfloxacin, tosufloxacin, levofloxacin, nitrofurantoin, furazolidone, nitrofural, metronidazole, tinidazole, berberine hydrochloride |
| Antituberculous drugs | rifampicin, rifandin, rifapentine, rifabutin, capreomycin, viomycin, cycloserine, isoniazid, ethambutol hydrochloride, aminosalicylate sodium, pyrazinamide |
| Antiviral drugs | aciclovir, valaciclovir, penciclovir, famciclovir, ganciclovir, valganciclovir, foscarnet sodium, cidofovir, fomivirsen, idoxuridine, trifluridine, vidarabine, brivudine, zanamivir, oseltamivir |
| Anti-neoplasm drugs | methotrexate, edatrexate, lometrexol, trimetrexate, piritrexim, aminopterin sodium, fluorouracil, tegafur, carmofur, floxuridine, uft, altretamine, doxifluridine, tegadifur, mercaptopurine, tioguanine, azaguanine, sulfomercaprine sodium, pentostatin, hydroxycarbamide, hydroxyguanidine, cytarabine, ancitabine, capecitabine, enocitabine, gemcitabine, fludarabine phosphate, chlorambucil, methoxymerphalan, mechlorethaminoxide, sarcolysin, nitrocaphane, betamerphalan, ocaphane, formylmerphalan, glyfosfin, improsulfan tosilate, dianhydrodulcitol, dopan, carmustine, procarbazine, uramustine, lomustine, pipobroman, uraphetin, semustine, razoxane, nimustine, ethylenediamine tetraacetylimide, mannomustine, ranimustine, mitomycin, estramustine phosphate, fotemustine, cisplatin, prednimustine, streptozocin, carboplatin, iproplatin, oxaliplatin, nedaplatin, lobaplatin, iridium platinum, thiotepa, chlorozotocin, solaziquone, pcnu, triaziquone, dacarbazine, diaziquone, etoglucid, carboquone, busulfan, treosulfan, mitobronitol,, mitolactol, monocrotaline, bleomycin sulfate, bleomycin a5, boanmycin hydrochloride, etoposide, teniposide, chromomycin a3, plicamycin, peplomycin, hycanthone, camptothecin, hydroxycamptothecin, irinotecan, topotecan, daunorubicin, doxorubicin hydrochloride, pirarubicin, epirubicin, idarubicin hydrochloride, zorubicin hydrochloride, aclarubicin, detorubicin, aclacinomycin b, menogaril, piroxantrone, mitoguazone hydrochloride, mitoxantrone, bisantrene hydrochloride, amsacrine, nitracrine hydrochloride, dactinomycin, asparaginase, colchicine, colchiceinamide, vinblastine, vincristine, vindesine, vinorelbine, paclitaxel, docetaxel, harringtonine, homoharringtonine, emetine hydrochloride, aminoglutethimide, mitotane, tamoxifen, exemestane, toremifene citrate, formestane, anastrozole, flutamide, letrozole, fadrozole, bicalutamide, nilutamide, leuprorelin acetate, goserelin acetate, triptorelin, sizofiran, arsenic trioxide, cantharidin, norcantharidin, methylcantharidimide, nocardia rubra-cell wall skeleton, tretinoin, porfimer sodium, rituximab, trastuzumab, bortezomib |
| Immunomodulators | ciclosporin, tacrolimus, sirolimus, everolimus, gusperimus hydrochloride, mizoribine, azathioprine, mycophenolate |

TABLE 2-continued

| Class of active agents | Exemplary active agents |
| --- | --- |
| | mofetil, FTY720, cyclophosphamide, methotrexate, antithymocyte globulin, muromonab-cd3, daclizumab, basiliximab, anti-Rh antibody, anakinra, leflunomide, pimecrolimus, tripterygium glycosides, bacillus calmette-guerin vaccine, corynebacterium parvum vaccine, picibanil, ubenimex, muramyl dipeptide, broncho-vaxom, romurtide, coriolus versicolor polysaccharide, lentinan, polyerga, biostim, transfer factor, thymosin, thymosinα1, thymopentin, levamisole, isoprinosine, ditiocarb sodium, pidotimod, polyinosinic acid-polycytidylic acid, polyactin a, aldesleukin, interferon |
| Cosmetically active agents | botulinum toxin, adenosin triphosphate (ATP), alpha glucosyl rutin, alpha hydroxy acids, alcohol, algae-extract, allantoin, aloe vera, amino acids, anti-ageing complex aquaspheres (vitamins E and F and unsaponifiables of olive oil), astringent agents avocado oil, aquaspheres, avocado oil, beeswax, beta-glucan, bio-cytokine, biodermin, biotin, bisabolol, butyl octanoic acid (BOA), borage oil, broadspectrum filter, burdock root extract, butcher's broom (*Ruscus aculeatus*, mausedorn), camellia kissi oil, ceramides, ceramide-lipid system, coconut oil, coenzyme Q, ubiquinone, coenzyme R, comfrey extract, contourmin (a complex based on barley extract and escin), corn flower extract, cornstarch derivate, crystal lipids, cucumber extract, cyclodermin, cyclodextrin, dihydroxyaceton (DHA), enzyme activating substances, juvena, erythru lose, erythulose, escin, essential fatty acids, eyebright extract, fatty acids, galactoarabian, gentian extract, ginseng extract, grape seed oil, hamamelis extract, hawkweed extract, Hibiscus esculentus seed extract, hibiscus flower acids, glycerin-acrylic acid polymer, ive transparent pigments, jojoba oil, kaolin, lactic acid, lecithin-complex (mixture of lecithin, phospholipid and other plant lipids), licorice extract, lipocer, algae extract, carnitin, coffein, lupin oil, lysin aspartat, macadamia oil, mallow extract, marine collagen, mate extract, nicotinic acid niacinamide, olive oil extract (unsaponifiables), pansy extract, pearlproteins, juvitacell, panthenol, pea extract, meadowfoam seed oil (limnanthes alba, sumpfblume), menthol, menthol derivative, mica pigments, microfine pigments, honey extract, micro proteins, mint extract, mulberry extract, mushroom extract, pearly pigments, peeling granules, phytoceramide phytosan, phytosterols, pineapple enzyme (bromelain), polymer pigments, hyaluronic acid, polysaccharides, prolactis, propantriol, proline, purcellin oil, peppermit oil, pyridoxin (vitamin 26), repair complex, saccharides, salicylic acid, silkprotein, huangquin root extract, subtilisin, shea butter, barley extract, mushroom extract, coffeine, soybean oil, soya proteins, squalan E, tanning accelerator tensides, titanum dioxide, tocopheryl acetate, vegetable proteins, extract from peas, vitamin A pure (retinol), vitamin A derivate, vitamin A palmitate, vitamin B6 (pyridoxine), vitamin C pure - vitamin C (l-ascorbic acid), vitamin C-derivative, vitamin A, vitamin C, vitamin E, vitamin F, vitamin H, vitamin H with salt of citric acid, water lily root extract, wheat proteins, extracts of mulberry (morus nigra), extracts of grapes (vitis vinifera) and extracts of baikal, skullcap (scutella baicalensis, helmetflower), wild mango butter, witch hazel extract, yeast extract |

C. Microparticles and Matrix

The controlled release composition comprises a plurality of microparticles operably linked to a matrix.

The plurality of microparticles comprises a first material and a first active agent. In certain embodiments, at least one of the plurality of the microparticles comprises a first material and a first active agent. The weight percentages of the first material and the first active agent in the microparticles can vary in any suitable ranges, and will be selected by a person skilled in the art as appropriate. In certain embodiments, at least one of the plurality of microparticles comprises a weight percentage of about 2% to about 98% of the first material, and about 2% to about 98% of the first active agent. In certain embodiments, at least one of the plurality of microparticles comprises a weight percentage of 20% to about 70% of the first material and about 30% to about 80% of the first active agent.

In certain embodiments, the plurality of microparticles further comprises a first additive. Any additives suitable for the purposes of the present disclosure known in the art can be used. In certain embodiments, the additive can be a pharmaceutically acceptable substance, composition or vehicle. The additives involve in modifying physical and/or chemical properties of the controlled release composition, regulating the release rate of the active agent, and/or approximate to the physiological conditions of the body.

Each additive is "pharmaceutically acceptable" in the sense of being compatible with the other ingredients, e.g. the materials and the active agent, of the controlled release composition and suitable for use in contact with the tissue or organ of a living organism without excessive toxicity, irritation, allergic response, immunogenicity, or other problems or complications, commensurate with a reasonable benefit/risk ratio.

Any additives suitable for the purposes of the present disclosure can be used, for example, rate modifying agents, antioxidants, colorants, buffers, aromatics, colorants, flavor-improving agents, sweeteners, fillers, lubricants, isotonic agents, antimicrobial agents, anesthetics, preservatives, homogenization agents, toxicity adjusting agents, excipients, powders, salines, or other additives known in the art, or various combinations thereof.

Suitable rate modifying agents include, for example, sodium crosscaramellose, sodium carboxymethylcellulose, powdered cellulose, colloidal silicon dioxide, crospovidone, depolymerizable guar gum, magnesium aluminum silicate, methyl cellulose, alginic acid, calcium carboxymethylcellulose, potassium polacrilin (and other cation exchange resins such as Amberlite resins), starch, pregelatinized starch, sodium starch glycolate, sodium alginate, inorganic salts (e.g., sodium chloride and potassium chloride), tweens, myrjs, sucrose, lactose, sorbitol, mannitol, fructose, glucose, dextran, fatty acid esters, inositol, magnesium stearate, zinc stearate, calcium stearate, gum Arabic, and sodium alginate.

Suitable antioxidants include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. The reduction in oxidation prevents or reduces loss of binding affinity, thereby improving stability of the composition and maximizing shelf-life.

Suitable fillers include, for example, talc, titanium dioxide, starch, kaolin, cellulose (microcrystalline or powdered) and combinations thereof.

Suitable buffers include, for example, sodium acetate, sodium chloride, potassium chloride, calcium chloride, sodium lactate and the like, for approximating the physiological conditions of the living organism.

Suitable lubricants include, for example, talc, calcium stearate, magnesium stearate, solid polyethylene glycols, sodium lauryl sulfate.

The weight percentage of the additive in the microparticles ranges from about 0% to about 30%. In certain embodiments, the weight percentage of the additive in the microparticles ranges from about 0% to about 20%.

In certain embodiments, the plurality of microparticles can be further provided with a coating. Without being bound to any theory, but it is believed that coating of microparticles can modify the mode of release of the active agent or modify the physical and/or chemical properties of the microparticles. For example, a coating modify the release rate of the active agent. For another example, a coating modify the opacity of the microparticles.

Any suitable coating substances can be used. In certain embodiments, the coating substance comprises a sugar. In certain embodiments, the coating substance comprises a polymer. In certain embodiments, the coating substance further comprises a plasticizer to make the polymer in the coating substance softer and more pliable. In certain embodiments, the coating substance of the plurality of microparticles comprises a polymer whose initial melting temperature is higher than the complete melting temperature of the second material contained in the matrix. In certain embodiments, the coating substance of the plurality of microparticles comprises a colorant to protect the microparticles against light exposure.

The weight percentage of the plurality of microparticles in the controlled release composition can vary in any suitable range. In certain embodiments, the controlled release composition comprises a weight percentage of about 1% to about 95% of the plurality of microparticles. In certain embodiments, the controlled release composition comprises a weight percentage of about 20% to about 80% of the plurality of microparticles.

The matrix of the controlled release composition comprises a second material. In certain embodiments, the matrix further comprises a second active agent. The second active agent in the matrix may or may not be the same as the first active agent in the plurality of microparticles. In certain embodiments, the matrix further comprises a second additive. In certain embodiments, the second additive may or may not be the same as the first additive contained in the plurality of microparticles.

The weight percentages of the matrix in the controlled release composition can vary in any suitable ranges. In certain embodiments, the controlled release composition comprises a weight percentage of 2% to about 98% of the second material. In certain other embodiments, the controlled release composition comprises a weight percentage of 20% to about 80% of the second material. In certain embodiments, the controlled release composition comprises a weight percentage of 0% to about 70% of the second active agent. In certain other embodiments, the controlled release composition comprises a weight percentage of 0% to about 30% of the second active agent. In certain embodiments, the controlled release composition comprises a weight percentage of 0% to about 30% of the second additive. In certain other embodiments, the controlled release composition comprise a weight percentage of 0% to about 20% of the second additive.

The plurality of microparticles can be operably linked to the matrix in the controlled release composition. The term "operably linked" or "operably linking", as used herein, includes embedding, incorporating, integrating, binding, combining, cross-linking, mixing, and/or coating microparticles to a matrix. In certain embodiments, the microparticles can be embedded in the matrix. In certain embodiments, the microparticles can be uniformly or randomly distributed or embedded in the matrix. In certain embodiments, the plurality of microparticles can be distributed or embedded in the matrix in accordance with a pre-determined pattern, such as, without limitation, a layered pattern. In certain embodiments, the matrix can be coated on the surface of the microparticles. In certain embodiments, a portion of the microparticles can be embedded within the matrix and the rest of the microparticles can be coated on the surface of the matrix. A schematic drawing in FIG. 14 shows a representative constitution of the controlled release composition.

In certain embodiments, the controlled release composition further comprises a coating. A coating can be decided by a person skilled in the art as appropriate, for example, a coating can be desired to modify the physiochemical properties of the controlled release composition (e.g. opacity) or to modify the release rate or release profile of the active agent from the composition.

The shape and size of the plurality of microparticles and/or the controlled release composition can be selected as appropriate by a person skilled in the art. The microparticles can be in any suitable shape known in the art, such as, without limitation, amorphous, tubular, platelet, granule, block, and membrane. The size of the plurality of microparticles can vary in a wide range. In certain embodiments, at least one of the plurality of microparticles has a size (diameter) ranging from about 1 to about 5000 μm. In certain embodiments, at least one of the plurality of microparticles has a size (e.g. diameter) ranging from about 20 μm to about 1000

The controlled release composition can be of any irregular shapes or regular shapes, such as, without limitation, pellets, pellet chains, rings, patches, membranes, granules, balls, blocks, needles, and cylinders. In certain embodiments, the controlled release composition can be in the shape of cylinders, membranes, pellets, or pellet chains.

The controlled release composition can be of any size compatible with the route of administration and the target site and can be selected as appropriate by a person skilled in the art. In certain embodiments, the controlled release composition can be of a size of about 0.2 mm to about 200 mm. For example, the controlled release composition can be of a cylinderical shape with a radius of about 0.2 mm to about 10 mm and a length of about 0.3 mm to about 20 mm, or a radius of about 0.3 mm to about 5 mm and a length of about 0.4 mm to about 10 mm. For another example, the controlled release composition can be of a membrane or patch shape with a radius of about 5.0 mm to about 150 mm and a thickness of about 0.1 mm to about 5 mm; a radius of about 10 mm to about 60 mm and a thickness of about 0.3 mm to about 2 mm; a length of about 5.0 mm to about 150 mm, a width of about 3.0 mm to about 100 mm, and a thickness of about 0.1 mm to about 5 mm; or a length of about 10 mm to about 100 mm, a width of about 5.0 mm to about 100 mm, and a thickness of about 0.3 mm to about 2 mm. For yet another example, the controlled release composition can be of a granule shape with a radius of about 0.5 mm to about 20 mm, or about 3.0 mm to about 10 mm.

In another aspect, the present disclosure provides a controlled release composition comprising a plurality of microparticles operably linked to a matrix, wherein the controlled release composition can be formed in accordance with the method comprising: preparing a plurality of microparticles comprising a first material and a first active agent; and applying the plurality of microparticles to a matrix-form ing composition thereby forming the controlled release composition.

II. Method of Preparation

In another aspect, the present disclosure provides a method for making the controlled release composition provided herein, comprising: preparing a plurality of microparticles comprising a first material and a first active agent; and applying the plurality of microparticles to a matrix-forming composition thereby forming the controlled release composition.

The plurality of microparticles provided herein can be prepared by any suitable methods known in the art. In certain embodiments, the microparticles can be prepared by providing the first material to the first agent, and forming the microparticles. The first material can be one or more polymer(s), one or more non-polymeric organic compound(s), or a combination of one or more polymer(s) and one or more non-polymeric organic compound(s). In certain embodiments, the microparticles can be prepared by providing the polymer-forming monomers to the first agent, and forming the microparticles. The polymer-forming monomers can be polymerized to form a polymer. In certain embodiments, the method of preparing the microparticles further comprises dividing the obtained product into the microparticles of desirable sizes.

In certain embodiments, microparticles can be prepared by mixing active agents, polymer-forming monomers, and optionally, additives and catalysts, and cross-linking the polymer-forming monomers to form the polymer, thereby entrapping the active agents within the polymer to form the microparticles. Monomers and methods and conditions suitable for forming polymers suitable for the purposes of the present disclosure are known in the art and can be selected by persons skilled in the art without undue experimentation. The polymerization conditions can be determined and adjusted as appropriate to form the polymer and the microparticles by a person skilled in the art. For example, the first active agent can be mixed with methacrylate monomers, and the mixture can be reacted in the presence of perbenzoic acid at 80° C. under normal atmospheric pressure to allow formation of poly(methacrylate) microparticles, which are incorporated with the first active agent.

Various methods known in the art can be used to prepare the microparticles, including, for example, coacervation method such as single coacervation and complex coacervation, emulsion solidification, solvent evaporation, solvent extraction, cross-linking method, hot-melt encapsulation, interfacial polymerization, spray drying, spray coating, fluid-bed coating, and pan coating, supercritical fluid method, double axis extrusion, and centrifugation based method (for review, please refer to: J. Swarbrick, Encyclopedia of pharmaceutical technology, Volume 4, Edition 3, published by Informa Health Care, 2007, p 2316-2325; S. Benita, Microencapsulation: methods and industrial applications, published by CRC Press, 2006, p 2-41). The methods of preparing microparticles can be selected by a person skilled in the art as appropriate, taking into consideration factors such as the desirable size of the microparticles, the physiochemical characteristics of the active agent and/or the first material, and the required equipments.

In one embodiment, microparticles can be prepared using a physicochemical process. For example, microparticles can be prepared by reducing the solubility of the first material in the first material solution/composition through adding a flocculant. Microparticles can also be prepared where materials with opposite charges are used as the composite materials, and the composite materials are cross-linked to encapsulate active agents into the resulting microparticles. Microparticles can also be prepared where a solvent capable of inducing phase separation is added into the first material composition/solution, causing the formation of microparticles. Microparticles can further be formed where the first material are melted or dissolved at a high temperature and then cooled. In addition, microparticles can be prepared eliminating volatile solvents (such as, by evaporation) in the dispersion phase of an emulsion composition. Furthermore, microparticles can be prepared by dissolving the first material and the first active agent in a solvent, followed by eliminating the solvent and grinding the particles formed.

In another embodiment, microparticles can be prepared using a physical mechanical process. For example, microparticles can be prepared using a spray drying process which involves applying the first active agent into the first material solution, followed by atomizing the mixture into hot inertia airflow. Droplets are formed, condensed, and dried to form microparticles. Microparticles can also be formed by using a spray cooling process where the first active agent and the frist material composition (e.g., a melted first material composition comprising the first active agent) is sprayed into a cooled airflow, resulting in the formation of microparticles. Microparticles can further be formed using a centrifugation-based process, a fluid bed coating-based process, or a supercritical fluid-based process. In addition, microparticles can be prepared using extrusion or a pan coating process, where the former involves blending the first active agent and the first material in an extruder, followed by kneading and grinding to form microparticles, and the later involves coating drug particles with materials.

In yet another embodiment, microparticles can be prepared using a chemical process. For example, microparticles can be prepared using an interfacial polycondensation process which involves a polycondensation reaction which occurs at the interface of a dispersed phase (e.g., water) and a continuous phase (e.g., organic phase). Microparticles can also be formed by using a radiation-based cross-linking process.

In still another embodiment, microparticles can be prepared using a melting process. For example, the first material, the first active agent, and optionally, additives can be mixed, and the mixture can be melted, cooled, and grinded to form microparticles. Microparticles can also be formed when melted first active agent and the first material mixture is added into a blender and cooled while being actively agitated. Microparticles can also be formed where melted first active agent and the first material mixture is applied onto the surface of a substrate (e.g., stainless steel) and rapidly cooled, and the resulting solids are crashed/grinded.

In certain embodiments, the prepared microparticles can be further coated, such as, without limitation, by using a pan coating process, or a fluid bed coating process (for review, please refer to: J. Swarbrick, Encyclopedia of pharmaceutical technology, Volume 4, Edition 3, published by Informa Health Care, 2007, p 2330-2331). For example, a coating can be desirable for making a controlled release composition having a release period of months or years.

The controlled release composition can be prepared by applying the plurality of microparticles to a matrix-forming composition. As used herein, the term "matrix-forming composition" refers to a composition comprising substances for forming a matrix, which includes, without limitation, the second material, a polymer, polymer-forming monomers, a non-polymeric organic compound, active agents, additives, catalysts, solvent, and/or combinations thereof. In certain embodiments, the method further comprises mixing the plurality of microparticles with a matrix-forming composition.

In certain embodiments, the matrix-forming composition comprises monomers for forming a polymer. In certain embodiments, the controlled release composition can be prepared by mixing the microparticles, polymer-forming monomers, and optionally, active agents, additives, and catalysts, and cross-linking the polymer-forming monomers to form the polymer, thereby entrapping the microparticles within the polymer network to form the matrix operably linked to the microparticles. Monomers, methods and conditions suitable for forming the polymer of the present disclosure can be selected by a person skilled in the art without undue experimentation.

In certain embodiments, the matrix-forming composition comprises the second material. The second material can be a polymer, a non-polymeric organic compound, or a combination of a polymer and a non-polymeric organic compounds. In certain embodiments, the controlled release composition can be prepared by mixing the microparticles, the second material, and forming the controlled release composition.

The controlled release composition can be prepared from the microparticles and the matrix-forming composition by any suitable techniques known in the art. Exemplary techniques include, without limitation, extrusion, extrusion moulding, injection molding, compression moulding, casting, coating, calendering and the like.

Extrusion method involves pushing or drawing the microparticles and the matrix-forming composition through a die of a desired cross-section. The extrusion process can be performed using an extruder such as a screw extruder, a sieve and basket extruder, a roll extruder and a ram extruder.

Extrusion moulding method involves extruding the microparticles and the matrix-forming composition and feeding the resulting material into a die to form a certain shape.

Injection molding method involves feeding the microparticles and the matrix-forming composition into a container and forcing them into a mold cavity.

Compression molding method involves placing microparticles and the matrix-forming composition in an open mold cavity, and applying pressure to the closed mold to force the material into contact with all mold areas.

Casting method involves pouring the microparticles and the matrix-forming composition into a mold cavity, and allowing the material to solidify. In certain embodiments, casting process can be preferred when making a controlled release composition having the shape of a patch or membrane.

Coating method involves applying a layer of matrix-forming composition on the surface of the microparticles.

Calendering method involves extruding the microparticles and the matrix-forming composition and forcing the resulting material to pass under rollers to take shape.

In certain embodiments, the method further comprises providing the shape for the controlled release composition. The shape of the controlled release composition can be of any irregular shapes or regular shapes, such as, without limitation, pellets, pellet chains, rings, patches, membranes, granules, balls, blocks, needles, and cylinders. Any suitable methods for providing shapes can be used. For example, the controlled release composition can be loaded to a syringe and pushed to pass through a needle to form cylindrical shaped controlled release composition.

In certain embodiments, the method of preparing the controlled release composition further comprises heating the microparticles and the matrix-forming composition to a predetermined temperature $T_m$, where $T_H > T_m > T_L$. It is desirable that at temperature $T_m$, the matrix forming composition is liquefied while the microparticles do not liquefy, and the liquefaction of the matrix forming composition can be reversed when cooled down. It is also desirable that at temperature $T_m$, the matrix forming composition does not decompose. If $T_L$ is the decomposition temperature of the second material, or if $T_L$ exceeds the decomposition temperature of one component of the second material, the controlled release composition can be prepared using methods other than heating the microparticles and the matrix-forming composition to a predetermined temperature $T_m$.

The temperature $T_m$ used in various embodiments of the present disclosure can be selected by a person skilled in the art without undue experimentation. For example, $T_m$ can be determined using the formula: $(T_H+T_L)/2$. In one embodiment, $T_m$ can be a temperature in a range of $(T_H+T_L)/2 \pm$ about 5° C., $(T_H+T_L)/2 \pm$ about 10° C., $(T_H+T_L)/2 \pm$ about 15° C., or $(T_H+T_L)/2 \pm$ about 20° C. In another embodiment, $T_m$ can be determined using the formula: $T_H-T_m \geq$ about 5° C., $T_H-T_m \geq$ about 10° C., $T_H-T_m \geq$ about 15° C., or $T_H-T_m \geq$ about 20° C. In yet another embodiment, $T_m$ can be determined using the formula: $T_m-T_L \geq$ about 5° C., $T_m-T_L \geq$ about 10° C., $T_m-T_L \geq$ about 15° C., or $T_m-T_L \geq$ about 20° C.

In still another embodiment, $T_m$ can be in a range from ($T_L$+ about 5° C.) to ($T_H$− about 5° C.), from ($T_L$+ about 10° C.) to ($T_H$− about 10° C.), from ($T_L$+ about 15° C.) to ($T_H$− about 15° C.), from ($T_L$+ about 20° C.) to ($T_H$− about 20° C.).

In certain embodiments, when the plurality of microparticles comprise a coating, the $T_m$ can be further selected to be below the initial melting temperature of the coating substance of the microparticles.

In certain embodiments, the method of preparing the controlled release composition further comprises dissolving the matrix-forming composition in a solvent. The solvent can be selected where the first material or the microparticles comprising the first material are insoluble or substantially insoluble in such solvent. In certain embodiments, the solvent can be evaporated to form the controlled release composition.

III. Method of Use

In another aspect, the present disclosure provides a method of treating and/or preventing a condition in a subject, comprising administering to the subject the controlled release composition provided herein.

The term "condition," as used herein, includes, without limitation, a pathological condition, a physiological condition, and a cosmetic condition. In certain embodiments, a condition, such as an aging-related condition, simultaneously be a pathological condition, a physiological condition, and a cosmetic condition.

Examples of pathological condition include without limitation, aging, angina, antithrombin deficiency, arrhythmia, atherosclerosis, artrial fibrillation, atrial flutter, blood clots, cardiacischemia, cardiac surgery, cardiomyopathy, cardiovascular abnormalities, carotid artery disease, chest pain, circulation disorders, claudication, collagen vascular diseases, congenital heart diseases, congestive heart failure, coronary artery disease, diabetes, diabetes and hypertension, dyslipidemia, dysrhythmia, elevated triglycerides, heart defect, heart disease, heart failure, heart valve disease, hemangioma, high cholesterol, hypertriglyceridemia, intermittent claudication, hypertension, Kawasaki disease, heart attack, myocardial ischemia, orthostatic hypotension, peripheral arterial disease, peripheral arterial occlusive disease, peripheral vascular disease, Raynaud's disease, smoking cessation, tachycardia (fast heart rate), thrombosis, varicose veins, vascular diseases, venous leg ulcers, gingivitis, gum diseases, halitosis, oral cancer, periodontal disease, temporomandibular disorders, temporomandibular joint syndrome, sunburn, acne, skin aging, alopecia, anesthesia, athlete's foot, atopic dermatitis, bed sores (decubitus ulcers), bunions, burns, burn infections, cold sores (herpes labialis infections), congenital skin diseases, contact dermatitis, cutaneous lupus erythematosus, diabetic foot ulcers, eczema, excessive sweating, fabry disease, fungal infections, genital herpes, genital warts, hair loss, hair removal, hand dermatitis, head lice, hemangioma, hereditary angioedema, herpes simplex infections, herpes Zoster infections, herpetic neuralgia, hives, ichthyosis, ischemic foot ulcers, keratoses, lupus, male pattern baldness, malignant melanoma, medical prosthetics, melanoma, molluscum contagiosum, mycosis fungoides, onychomycosis, pemphigus vulgaris, postherpetic neuralgia, pressure ulcers, psoriasis and psoriatic disorders, psoriatic arthritis, razor bumps, rosacea, sarcoidosis, scalp disorders, scar tissue, scleroderma, seborrhea, seborrheic dermatitis, shingles, skin cancer, skin infections, skin lipomas, skin wounds, solar lentigines, sporotrichosis, staphylococcai skin infections, stasis dermatitis, stretch marks, systemic fungai infections, sun poisoning, ringworm, tinea capitis, tinea *versicolor*, urticaria, vitiligo, warts, wounds, acromegaly, adrenal cancer, congenital adrenal hyperplasia, diabetes mellitus (type I and type II), diabetes mellitus (type I), diabetes mellitus (type II), diabetic gastroparesis, diabetic kidney disease, diabetic macular edema, diabetic neuropathy, diabetic retinopathy, diabetic vitreous hemorrhage, dyslipidemia, female hormonal deficiencies/abnormalities, Fredrickson type III. hyperlipoproteinemia, growth hormone deficiencies/abnormalities, gynecomastia, hair removal, hyperlipidemia, hormone deficiencies, hot flash, hyperparathyroidism, idiopathic short stature, indication: diabetes type II, male hormonal deficiencies/abnormalities, McCune-Albright syndrome, menopause disorders, metabolic syndrome, obesity, ovarian cancer, pancreatic cancer, pancreatic disorders, pancreatitis, parathyroid cancer, parathyroid disease, parathyroid disorders, perimenopause, pituitary disorders, polycystic ovarian syndrome, post menopause disorders, post menopause osteopenia, precocious puberty, primary insulin hypersecretion, severe short stature, sexual dysfunction, thyroid disease, thyroid disorders, Turner syndrome, Wilms' tumor, Wilson's disease, abdominal cancer, achalasia, alpha 1 antitrypsin deficiency, anal fissures, appendicitis, Barrett's esophagus, biliary tract cancer, bowel dysfunction, celiac disease, chronic diarrhea, clostridium difficile-associated diarrhea, colon cancer, colon polyps, colorectal cancer, constipation, Crohn's disease, diabetic gastroparesis, digestive system neoplasms, duodenal ulcers, Fabry disease, fecal incontinence, functional dyspepsia, gall bladder disorders, gastric cancer, gastric ulcers, gastroenteritis, gastroesophageal reflux disease, gastrointestinal disease and disorders, gastroparesis, heartburn, helicobacter pylori, hemorrhoids, hepatic encephalopathy, hepatitis, ileus, infectious colitis, inflammatory bowel disease, intra-abdominal infections, irritable bowel syndrome, liver disease, liver disorders, non-erosive reflux disease, non-ulcer dyspepsia, organ rejection following organ transplantation, post-operative nausea and vomiting, vomiting, rectal cancer, rectal disorders, recurrent diarrhea, stomach cancer, stomach discomfort, ulcerative colitis, abnormal blood vessels, acute myelogenous leukemia, anemia, anemia (non-Hodgking lymphoma), non-small-cell lung cancer, anemic cancer, aneurysm, antiphospholipid syndrome, antithrombin deficiency, aplastic anemia, blood clots, candidemia/candidiasis, chronic renal anemia, Gaucher disease, hematologic cancer, hematological disorders, paroxysmal hemoglobinuria, hemorrhages, hypercalcemia, hypogammaglobulinemia, hyponatremia, idiopathic thrombocytopenic purpura, islet cell cancer, leukemia, B-cell lymphoma, lymphomas, multiple myelomas, myelodysplastic syndromes, myocardial ischemia, occlusions, platelet deficiencies, platelet disorders, red cell disorders, renal anemia, sezary syndrome, sickle cell disease, T-cell lymphoma, thalassemia, thrombocytopenia, von Willebrand's disease, white cell disorders, acquired immune deficiency syndrome (AIDS), AIDS related infections, acute rhinitis, allergies, asthma, anal dysplasia, bacterial infections, canker sores, celiac disease, cervical dysplasia, chickenpox, chronic fatigue syndrome, common cold, common variable immunodeficiency, bacterial conjunctivitis, chronic obstructive pulmonary disease, cutaneous candidiasis, cutaneous T-cell lymphoma, cytomegalovirus infections, dermatomyositis, fever, graft-versus-host disease, hepatitis, hepatitis B, hepatitis C, HIV infections, HIV/AIDS, human papilloma virus infections, hypogammaglobulinemia, idiopathic inflammatory myopathies, influenza, intra-abdominal infections, Kaposi's sarcoma, lupus, lyme tick disease, mycobacterium avium complex infection, meningitis, onychomycosis, oral candidiasis, pneumonia, polymyositis (inflammatory muscle disease), postherpetic neuralgia, primary immunodeficiency disorders, respiratory syncytial virus infection, rheumatic fever, allergic rhinitis, rotavirus infection, sarcoidosis, sepsis and septicemia, sexually transmitted diseases, shingles, Sjogren's syndrome, smallpox, soft tissue infections, staphylococcal infections, staphylococcal skin infections, strep throat, systemic candidiasis, systemic lupus erythematosus, throat and tonsil infections, urticaria, vancomycin resistant enterococci, west nile virus infections, acromegaly, ankylosing spondylitis, bone loss, athletic injuries, bone diseases, bone metastases, breast pain, bunions, bursitis, carpal tunnel syndrome, cartilage injuries, chest pain, chronic back pain, chronic leg pain, chronic pain, chronic shoulder pain, claudication, congenital lactic acidosis, connective tissue diseases, dermatomyositis, dupurtren's disease, fibromyalgia, Frozen shoulder, adhesive capsulitis, gout (hyperuricemia), idiopathic inflammatory myopathies, intermittent claudication, joint injuries, knee injuries, multiple sclerosis, muscle pain, muscular dystrophy, musculoskeletal diseases, myasthenia gravis (chronic weakness), myasthenia gravis generalized, orthopedics, osteoarthritis, osteomyelitis, osteoporosis, osteosarcoma, Paget's disease, partial medial meniscectomy, parathyroid disease, post-menopausal osteopenia, post-menopausal osteoporosis, reflex sympathetic dystrophy syndrome, rheumatoid arthritis, sciatica, spinal cord disorders, spinal cord malignancy, spine athroplasty, sprains, tendon injuries, tennis elbow, tic disorders, anal dysplasia, benign prostatic hyperplasia, bladder cancer, bladder disorders, blood cancers, catheter complications, chronic pelvic pain, diabetic kidney disease, enuresis, erectile dysfunction, fabry disease, nocturia, genitourinary prolapse, glomerulonephritis, glom erulosclerosis, idiopathic membranous nephropathy, impotence, interstitial cystitis, kidney cancer, kidney disease, kidney failure, kidney stones, liver cancer, low testosterone, mastectomy, medical prosthetics, nephropathy, Peyronie's disease, premature ejaculation, prostate cancer, prostate disorders, prostatic intraepithelial neoplasia, proteinuria, Reiter's syndrome, renal artery disease, renal cell carcinoma, renal failure, testicular cancer, tyrosinemia, urethral strictures, urinary incontinence, urinary tract infections, urothelial tract cancer, male erectile dysfunction and female sex dysfunction, systemic blood pressure, abortion, hypotensive control, inhibition of platelet aggregation, pulmonary diseases, gastrointestinal disease, inflammation, shock, reproduction, fertility, bone loss, bone fractures, osteoporosis, metastatic bone disease, Paget's disease, periodontal disease, cartilage degeneration, endometriosis, uterine fibroid disease, hot flashes, increased levels of LDL cholesterol, cardiovascular disease, impairment of cognitive functioning, cerebral degenerative disorders, restenosis, gynecomastia, vascular smooth muscle cell proliferation, obesity, incontinence, anxiety, depression resulting from an estrogen deficiency, perimenopausal depression, post-partum depression, premenstrual syndrome, manic depression, anxiety, dementia, obsessive compulsive behavior, attention deficit disorder, sleep disorders, irritability, impulsivity, immune deficiency, auto immune diseases, anger management, multiple sclerosis and Parkinson's disease, inflammation, inflammatory condition, inflammatory bowel disease, respiratory diseases, sexual dysfunction, hypertension, retinal degeneration, asthma, cancers, rheumatoid arthritis, chronic inflammatory disorders, diabetes, chronic pain, central nerves system diseases, cardiovascular diseases, renal disease, reproductive diseases, infections, epilepsy, microcirculation improvement, drug withdrawal syndrome, bone marrow disease, edema, or a pathological condition related to a position in a subject (e.g., a human, an animal) which could be reached by an endoscope.

In certain embodiments, the pathological condition can be a cancerous condition. Cancerous conditions and tumor types that can be treated using the controlled release composition disclosed herein include but are not limited to carcinoma, blastoma, sarcoma, germ cell tumor, or hematological or lymphoid malignancy such as leukemia, lymphoma, or multiple myeloma. More specifically, cancerous conditions and tumor types that can be treated using the controlled release composition disclosed herein include but are not limited to squamous cell cancer, lung cancer (e.g., small cell lung cancer, non-small cell lung cancer (NSCLC), adenocarcinoma of the lung, or squamous cell carcinoma of the lung), cancer of the peritoneum, liver cancer (e.g., hepatocellular carcinoma/hepatoma), gastric or stomach cancer (e.g., gastrointestinal cancer), pancreatic cancer, brain tumor (e.g., glioblastoma/glioblastoma multiforme (GBM), non-glioblastoma brain tumor, or meningioma), glioma (e.g., ependymoma, astrocytoma, anaplastic astrocytoma, oligodendroglioma, or mixed glioma such as oligoastrocytoma), cervical cancer, ovarian cancer, uterine cervix cancer, liver cancer (e.g., hepatoblastoma, hepatocellular carcinoma/hepatoma, or hepatic carcinoma), bladder cancer (e.g., urothelial cancer), breast cancer, colon cancer, colorectal cancer, rectal cancer, endometrial or uterine carcinoma, salivary gland carcinoma, esophageal carcinoma, kidney or renal cancer (e.g., rhabdoid tumor of the kidney), prostate cancer, vulval cancer, penile cancer, anal cancer (e.g., anal squamous cell carcinoma), thyroid cancer, parathyroid carcinoma, head and neck cancer (e.g., nasopharyngeal cancer, corpus linguae tumor, gingival neoplasm, and tonsillar tumor,), skin cancer (e.g., melanoma or squamous cell carcinoma), osteosarcoma, osteocarcinoma, osteoma sarcomatosum, Ewing's sarcoma, chondrosarcoma, soft tissue sarcoma (e.g., rhabdomyosarcoma, fibrosarcoma, Kaposi's sarcoma), carcinoid cancer, eye cancer (e.g., retinoblastoma), mesothelioma, lymphocytic/lymphoblastic leukemia (e.g., acute lymphocytic/lymphoblastic leukemia (ALL) of both T-cell lineage and B-cell precursor lineage, chronic lymphoblastic/lymphocytic leukemia (CLL), acute myelogenous/myeloblastic leukemia (AML), including mast cell leukemia, chronic myelogenous/myelocytic/myeloblastic leukemia (CML), hairy cell leukemia (HCL), Hodgkin's disease, non-Hodgkin's lymphoma, chronic myelomonocytic leukemia (CMML), follicular lymphoma (FL), diffuse large B cell lymphoma (DLCL), mantle cell lymphoma (MCL), Burkitt's lymphoma (BL), mycosis fungoides, Sezary syndrome, cutaneous T-cell lymphoma, mast cell neoplasm, medulloblastoma, nephroblastoma, solitary plasmacytoma, myelodysplastic syndrome, chronic and non-chronic myeloproliferative disorder, central nervous system tumor, pituitary adenoma, vestibular schwannoma, primitive neuroectodermal tumor, ependymoma, choroid plexus papilloma, polycythemia vera, thrombocythemia, idiopathic myelfibrosis, and pediatric cancers such as pediatric sarcomas (e.g., neuroblastoma, rhabdomyosarcoma, and osteosarcoma). In addition, tumors can be malignant (e.g., cancers) or benign (e.g., hyperplasia, cyst, pseudocyst, hamartoma, and benign neoplasm).

Examples of physiological conditions include without limitation, aging, contraception, wound healing, and post surgical adhesion.

Examples of cosmetic condition include without limitation, skin aging (e.g. wrinkling, loss of elasticity, sagging, uneven pigmentation, and loss of underlying tissue mass), cosmetic defect (e.g. striae gravidoram, striae distensiae, atrophic scarring, wound or surgical scarring, or hair loss), undesired pigmentation, or post-cosmetic procedure damage resulted from, for example, chemical peel, dermabrasion, laser resurfacing, ablative resurfacing, nonablative resurfacing, photodynamic therapy, noncoherent light phototherapy, breast lift, face lift, eyelid lift, forehead lift, neck lift, thigh lift, buttock lift, tummy tuck, and scar revision.

The controlled release composition disclosed herein can be administered to a target site via any suitable methods. The term "target site" refers to the site in a living organism where a condition occurs. By delivering the controlled release composition to the target site, the active agent contained in the controlled release composition can be released in a controlled fashion in proximity of the target site, and acts to alleviate or treat the condition. In certain embodiments, the controlled release composition can be surgically implanted, injected, administered via percutaneous puncture, introduced through a body opening, or topically applied to a target site.

In certain embodiments, the controlled release composition can be surgically implanted to the target site. For example, in an open surgery, the controlled release composition can be spread by hand or be placed by a device such as forceps or the like to a tissue in need such as brain or kidney. For another example, the controlled release composition can be injected via a specialized needle into a target site such as a solid tumor during surgery. For yet another example, the controlled release composition can be inserted into a cavity or an incision during a surgery. In certain embodiments, the controlled release composition can be further fixed to the target site, for example, with protein-based glue, or biodegradable gauze.

In certain embodiments, the controlled release composition can be injected to the target site. The injection can be performed using a syringe and a needle. The controlled release composition can be injected to the target site via any suitable routes such as subcutaneous, intraperitoneal, intramuscular, intradermal, intranasal, or intraocular injection. For example, the pellet shaped controlled release composition can be injected into muscle tissues. For another example, the controlled release composition suitable for injection can be injected subcutaneously.

In certain embodiments, the controlled release composition can be administered via percutaneous puncture. The puncture needle can be guided to the target site by using imaging techniques such as ultrasound, fluoroscopy, computed tomography (CT) or laser. Once the puncture needle reaches the target site, the controlled release composition can be delivered via the needle. The puncture route can be straight forward to the target site, and should avoid disruption of nerves or blood vessels. The controlled release composition can be administered via percutaneous puncture to any suitable target site, such as for example, kidney, lung and lumbar.

In certain embodiments, the controlled release composition can be introduced through a body opening. The body opening can be a natural body opening such as mouth, or can be an incision in a body cavity such as an incision in chest or abdomen. In certain embodiments, the controlled release composition can be inserted into a target site directly through the body opening. For example, the controlled release composition can be inserted into a cavity such as the periodontal, oral, vaginal, rectal or nasal cavity, a pocket such as a periodontal pocket or the eye, with or without creating an incision at the site. In certain embodiments, the controlled release composition can be delivered to the target site by hand. In certain embodiments, the controlled release composition can be delivered to the target site by an applicator. An applicator can be used when it is difficult to deliver the controlled release composition to the target site by hand, or when it is not convenient to place a uniform layer of the controlled release composition at the target site. Any suitable applicator can be used. For example, an applicator can be loaded with the controlled release composition in one end and operable to release the composition at the other end. In certain embodiments, the controlled release composition can be placed on the surface of an implantable device, such as a stent, and the implantable device can be placed to the target site to allow delivery of the controlled release composition. For example, the controlled release composition can be placed on the surface of an esophageal stent which is then placed at the diseased site of the esophagus. In certain embodiments, the controlled release composition can be introduced through a body opening via a delivery device. Suitable delivery device includes, for example, endoscope, delivery catheter, a surgically placed drain or access port or other applicators such as a needle. The delivery device can be introduced through a body opening and provide an access route to the target site to allow delivery of the controlled release composition to the particular site. In certain embodiments, the delivery device can be used in combination. For example, endoscope and implantation needle can be used in combination to allow introduction of the controlled release composition inside a cancerous tissue in pancreatic gland. The controlled release composition can be delivered via a delivery device to a body tract, cavity, or organ, such as for example, gastrointestinal tract (e.g. esophagus, stomach and duodenum, small intestine, large intestine, colon, bile duct, rectum), respiratory tract (e.g. nose, lower respiratory tract), ear tract, urinary tract, female reproductive system (e.g. cervix, uterus, fallopian tubes), abdominal or pelvic cavity, eye, interior of a joint, heart, lung, amnion, fetus, breast, and spine.

In certain embodiments, the controlled release composition can be topically applied to a target site. For example, the controlled release composition can be applied to the surface with or without fixation, for example without limitation, with glue or gauze. For another example, the controlled release composition can be dripped or brushed on the surface of the target site.

The controlled release composition can be administered to a subject at a dosage and for a release period. The dosage of the controlled release composition can be selected or adjusted by a person skilled in the art as sufficient for release of the active agent for a selected release period.

In certain embodiments, the dosage of the controlled release composition can be sufficient for release of a therapeutically effective amount of the active agent for the selected release period. The term "therapeutically effective amount" refers to the concentration of the active agent at the target site or in the blood, which concentration is effective to treat or prevent the target condition yet to allow the subject to tolerate such concentration without showing significant adverse effects. The therapeutically effective amount will depend on various factors known in the art, such as for example extent of the condition, the effect desired, state of health of the subject, potential for cross-reaction, allergies, sensitivities and adverse side-effects, past medical history, present medications, body weight and age.

In certain embodiments, the released amount of the active agent from the controlled release composition can be significantly less than (e.g. 10%, 20%, 30%, 40%, 50%, 60%, 70%, 80%, or 90% less than) the clinically approved dosage for systemic administration for the same period, while reaching similar local concentration. For example, the controlled release composition loaded with 5 clinically approved daily dosages for systemic administration can be sufficient for a release period of 10 days while achieving similar local concentrations and similar clinical effects. For another example, the controlled release composition administered at a dosage of 5 mg/kg (in terms of active agent) for a release period of two weeks can achieve a tumor inhibition rate of 20%, while systemic administration of the active agent at a dosage of 12 mg/kg for four consecutive doses in two weeks achieved a tumor inhibition rate of 19%.

In certain embodiments, the released amount of the active agent from the controlled release composition can be significantly less than (e.g. 10%, 20%, 30%, 40%, 50%, 60%, 70%, 80%, or 90% less than) the clinically approved dosage for systemic administration for the same period, while achieving even better local concentrations and better clinical outcome. For example, the controlled release composition administered at a dosage of 10 mg/kg (in terms of active agent) for a release period of two weeks can achieve a tumor inhibition rate of 37%, while systemic administration of the active agent at a dosage of 12 mg/kg for four consecutive dosages in two weeks achieved a tumor inhibition rate of 19%.

The release rate of the active agent from the controlled release composition can be varied due to different material properties, such as the type of the materials, the molecular weight of the materials, the molar fraction ratio of the monomers in a copolymer, the percentage of a certain material in the composition, and etc. The release of the active agent can last over a prolonged duration of time equal to or greater than about 1 day up to about 10 years after administration, for example, from about 1 day to about 5 years after administration, from about 1 day to about 2 years after administration, from about 1 day to about 2 years after administration, from about 1 day to about 1 year after administration, from about 1 day to about 6 months after administration, from about 1 day to about 3 months after administration, from about 1 day to about 1 month after administration, from about 1 day to about 2 weeks after administration, from about 1 day to about 1 week after administration, from about 1 day to about 5 days after administration, from about 1 month to about 2 years after administration, from about 2 months to about 2 years after administration, from about 3 months to about 2 years after administration, from about 6 months to about 2 years after administration, and from about 1 year to about 2 years after administration.

The release of the active agent from the controlled release composition can be in a time-dependent manner. In certain embodiments, the controlled release composition releases, in the first 3 days after administration, about less than 85% of the total amount of the active agent, about less than 80% of the total amount of the active agent, about less than 70% of the total amount of the active agent, about less than 60% of the total amount of the active agent, about less than 50% of the total amount of the active agent, about less than 40% of the total amount of the active agent, or about less than 30% of the total amount of the active agent. In certain embodiments, the controlled release composition releases, in the first 10 days after administration, about less than 75% of the total amount of the active agent, about less than 70% of the total amount of the active agent, about less than 65% of the total amount of the active agent, about less than 60% of the total amount of the active agent, about less than 55% of the total amount of the active agent, about less than 50% of the total amount of the active agent, about less than 45% of the total amount of the active agent, about less than 40% of the total amount of the active agent, about less than 35% of the total amount of the active agent, or about less than 30% of the total amount of the active agent.

Without being bound by theory, it is believed that the release of the active agent can be achieved by erosion and/or swelling of the material(s), and diffusion of the active agent from the microparticles and/or from the matrix to the target tissue. The release of the active agent can be influenced by factors such as the weight percentage of microparticles, the size and shape of the microparticles, the size and shape of the controlled release composition, the physiochemical properties of the active agent, and the erosion and/or swelling rate of the materials. These factors can be adjusted and/or selected to suit the purpose of treatment.

In certain embodiments, the weight percentage of the plurality of microparticles in the controlled release composition can be selected based on the purpose of treatment and/or the biological system's needs. For example, controlled release composition with a relatively higher percentage of microparticles can be used in treatment of various diseases. For another example, controlled release composition with a relatively lower percentage of microparticles can be used in anti-adhesion treatment during surgical operation, or can be used for sustained delivery of low-dose active agents such as hormones.

In certain embodiments, the size of the microparticles can be selected based on factors such as the release profile intended to achieve, the physiochemical properties of the first active agent, and the particular purpose of treatment. For example, microparticles with a diameter ranging from about 50 μm to about 150 μm can be used to prepare a controlled release composition designed for less than 10-day release period. For another example, microparticles with a diameter ranging from about 120 μm to about 1000 μm can be used to prepare a controlled release composition designed for more than 10-day release period. For yet another example, microparticles with a diameter ranging from about 50 μm to about 150 μm can be used to prepare a controlled release composition containing a hydrophobic drug as the first active agent designed for more than 10-day release period. For still another example, microparticles with a diameter ranging from about 50 μm to about 150 μm can be used to prepare a controlled release composition designed for anti-adhesion treatment during surgical operation.

The suitable shape of the controlled release composition can be selected based on factors such as the desired route of administration, purpose of treatment, and ease of handling. For example, the cylinder shaped controlled release composition can be suitable for administering drug through percutaneous puncture or endoscopy, or during operation. For another example, the patch shaped controlled release composition can be suitable for prevention of post surgery adhesion. For yet another example, the ball shaped controlled release composition can be suitable for use in induction.

In certain embodiments, the controlled release composition can be administered at a suitable frequency, such as for example, once a week, twice every three weeks, once every month, once every two months, once every six month, once a year, and once every two years.

Advantages

The controlled release compositions disclosed herein provide a variety of desired properties. As a controlled release formulation, the composition provided herein offers clinical or practical advantages over the conventional dosage forms. In certain embodiments, controlled release composition provided herein can be administered in a significantly lower dosing frequency. The release period of the active agent in the controlled release compositions reaches weeks, months or even years, and thus reduce the necessity of frequent dosing and improve patient's compliance. In certain embodiments, the controlled release compositions maintain a steady concentration of the active agent for a prolonged time, and achieve a more uniform pharmacological response.

In certain embodiments, the controlled release compositions can be administered locally where a condition occurs without the necessity of a systematic administration. A local administration of a controlled release composition allows an active agent to reach the same level of local concentration with a much lower dosage than that required in systematic administration of the active agent. In addition, local administration of the composition achieves a higher level of local concentration which can not be afforded in the systematic administration, or if possible, requires significantly higher dosage of the active agent in the systematic administration. The high local concentration of the active agent enables the treatment of a condition more effectively or much faster than a systematically delivered active agent and the treatment of new conditions that can not be possible or observed before. In the meantime, local administration of the controlled release composition can have significantly lower systemic exposure of the active agents than systemic administration has, and therefore can reduce potential sufferings from a systemic administration, for example, adverse reactions associated with the systematic exposure to the active agent, and/or gastrointestinal/renal effects.

In certain embodiment, the controlled release composition contains biodegradable materials which biodegrades in vivo and thus does not need to be surgically removed after the depletion of the active agent in the composition. The biodegradable materials breaks down or degrades into non-toxic components in vivo, without causing harm to the body.

In certain embodiments, when locally administered, the controlled release composition can be easily taken out from the subject after a period of time. This enables adjustment of dosage during treatment so as to better fit the physical state of the subject. The sample taken out from the subject also enables the measurement of the release curve, the investigation of the pharmacokinetic properties of the controlled release composition, and the generation of data required to obtain regulatory approval of the use of the controlled release composition.

In addition, compared to traditional microparticle-based controlled release compositions, the controlled release compositions of the present disclosure have a variety of improved physical, chemical, and/or pharmaceutical properties, e.g., without limitation, are more stable, have longer shelf life, require no solvent reconstitution, and are less prone to leaking when implanted (such as, when implanted into a solid tumor).

The present disclosure is described in the following Examples, which are set forth to aid in the understanding of the invention, and should not be construed to limit in any way the scope of the invention as defined in the claims which follow thereafter.

EXAMPLES

Example 1

Preparation of fluorouracil microparticles: 6.0 g fluorouracil and 4.0 g poly(L-lactic acid) (MW 20,000; melting range 162-168° C.) were mixed and melted at 170° C. The melted mixture was cooled and the resulting solid was grinded to yield the fluorouracil microparticles (size: about 180 μm).

Preparation of fluorouracil implants: 20.0 g poly (L-lactic-glycolic acid) (75/25; MW 16,000; melting range 68-76° C.), 12.0 g fluorouracil, and 8.0 g fluorouracil microparticles were mixed and extruded at 110° C. Cylindrical granules about ϕ 0.9 mm×4 mm in size were prepared (fluorouracil content: 42.0%).

Thirty Kunming mice were randomized into 5 groups with 6 mice in each group. One fluorouracil implant was implanted into the medial hind leg muscle of each mouse. Samples were collected at time points as indicated in Table 3. In vivo cumulative release of fluorouracil by the implants was measured. And the results are as shown in Table 3.

TABLE 3

| | Time | | | | |
|---|---|---|---|---|---|
| | 1 day | 5 days | 15 days | 30 days | 50 days |
| Cumulative release (%) | 11.6% | 37.3% | 60.4% | 74.1% | 93.3% |
| RSD % | 42.0% | 26.6% | 18.8% | 11.1% | 16.4% |

Example 2

Preparation of fluorouracil microparticles: 6.0 g fluorouracil, 3.0 g poly (L-lactic acid) (MW 20,000; melting range 162-168° C.), and 1.0 g dextran (40) were mixed and melted at 170° C. The melted mixture was cooled and the resulting materials were grinded to yield the fluorouracil microparticles (size: about 180 μm).

Preparation of fluorouracil implants: 17.0 g poly (L-lactic-glycolic acid) (75/25; MW 16,000; melting range 68-76° C.), 3.0 g polyethylene glycol, 12.0 g fluorouracil, and 8.0 g fluorouracil microparticles were blended. Cylindrical granules about ϕ 0.9 mm×4 mm in size were prepared by injection molding at 110° C. Fluorouracil content in the implants was 42.0%.

Thirty Kunming mice were randomized into 5 groups with 6 mice in each group. 1-2 pieces of fluorouracil implants were implanted into the medial hind leg muscle of each mouse. Samples were collected at time points as indicated in Table 4. In vivo cumulative release of fluorouracil by the implants was measured. And the results are as shown in Table 4.

TABLE 4

| | Time | | | | |
|---|---|---|---|---|---|
| | 1 day | 5 days | 10 days | 15 days | 20 days |
| Cumulative release (%) | 26.8% | 52.4% | 69.1% | 80.3% | 92.8% |
| RSD % | 30.5% | 18.8% | 22.3% | 13.0% | 9.7% |

Example 3

Preparation of etoposide microparticles: 6.0 g dextran (40) was dissolved in 75% ethanol, followed by the addition of 10.0 g etoposide to create a mixture. Ethanol was evaporated from the mixture to form a paste, which was dried (80°

C., −100 KPa, 8 hours) and grinded to yield etoposide microparticles (size: about 150 μm).

Preparation of etoposide implants: 3.0 g poly(L-lactic acid) (MW 20,000; melting range 162-168° C.) and 1.0 g polyethylene glycol (4000) were dispersed in ethanol. The mixture is desiccated and grinded to prepare microparticles of 150 μm in size. The microparticles were weighed, and mixed with etoposide microparticles at a ratio of 1:4 (w/w), respectively. The mixture was compressed to prepare cylindrical granules of ϕ 0.9 mm×2 mm in size. Etoposide content in the prepared etoposide implants was 50.0%.

Thirty Kunming mice were randomized into 5 groups with 6 mice in each group. One etoposide implant was implanted into the medial hind leg muscle of each mouse. Samples were collected at time points as indicated in Table 5. In vivo cumulative release of etoposide by the implants was measured. And the results are as shown in Table 5.

TABLE 5

| | Time | | | | |
|---|---|---|---|---|---|
| | 1 day | 5 days | 10 days | 15 days | 20 days |
| Cumulative release (%) | 20.8% | 50.5% | 69.9% | 82.2% | 94.7% |
| RSD % | 23.1% | 16.8% | 17.6% | 15.2% | 12.7% |

Example 4

Preparation of cisplatin microparticles: 5.0 g poly(L-lactic acid) (MW 20,000; melting range 162-168° C.) was dissolved in chloroform, followed by the addition of 5.0 g cisplatin. The mixture was well-stirred and the solvent was evaporated. The resulting material was grinded and sieved to prepare cisplatin microparticles (size: about 250 μm).

Preparation of cisplatin implants: 21.0 g poly(L-lactic-glycolic acid) (75/25; MW 16,000; melting range 68-76° C.), 6.0 g polyethylene glycol (4000), 7.0 g cisplatin, and 6.0 g cisplatin microparticles were mixed and extruded at 110° C. to prepare cylindrical granules of ϕ 0.9 mm×2 mm in size. Cisplatin content in the prepared cisplatin microparticles was 25.0%.

Thirty Kunming mice were randomized into 5 groups with 6 mice in each group. One cisplatin implant was implanted into the medial hind leg muscle of each mouse. Samples were collected at time points as indicated in Table 6. In vivo cumulative release of cisplatin by the implants was measured. And the results are as shown in Table 6.

TABLE 6

| | Time | | | | |
|---|---|---|---|---|---|
| | 1 day | 5 days | 10 days | 20 days | 35 days |
| Cumulative release (%) | 17.3% | 38.9% | 55.3% | 66.7% | 80.2% |
| RSD % | 28.4% | 24.7% | 19.6% | 13.5% | 8.7% |

Example 5

Preparation of cisplatin microparticles: 5.0 g poly(L-lactic acid) (MW 20,000; melting range 162-168° C.) was dissolved in chloroform, followed by the addition of 5.0 g cisplatin. The mixture was well-stirred and the solvent were evaporated. The resulting material was grinded and sieved to prepare cisplatin microparticles (size: about 125 μm).

Preparation of cisplatin implants: 21.0 g poly (L-lactic-glycolic acid) (75/25; MW 16,000; melting range 68-76° C.), 6.0 g polyethylene glycol (4000), 7.0 g cisplatin, and 6.0 g cisplatin microparticles were mixed and extruded at 110° C. to prepare cylindrical granules of ϕ 0.9 mm×2 mm in size. Cisplatin content in the cisplatin microparticles was 25.0%.

Thirty Kunming mice were randomized into 5 groups with 6 mice in each group. One cisplatin implant was implanted into the medial hind leg muscle of each mouse. Samples were collected at time points as indicated in Table 7. In vivo cumulative release of cisplatin by the implants was measured. And the results are as shown in Table 7.

TABLE 7

| | Time | | | | |
|---|---|---|---|---|---|
| | 1 day | 5 days | 10 days | 20 days | 30 days |
| Cumulative release (%) | 22.6% | 43.7% | 65.3% | 78.7% | 85.4% |
| RSD % | 33.5% | 26.1% | 19.6% | 13.5% | 6.6% |

Example 6

Preparation of dexamethasone microparticles: 4.0 g dextran (40) was dissolved in 75% ethanol, followed by the addition of 10.0 g dexamethasone to create a mixture. Ethanol was evaporated to form a paste, which was desiccated (80° C., −100 KPa, 8 hours), and grinded to prepare dexamethasone microparticles (size: about 150 μm).

Preparation of dexamethasone implants: 5.0 g poly (L-lactic acid) (MW 20,000; melting range 162-168° C.) and 1.0 g polyethylene glycol (4000) were dispersed in ethanol. The mixture was desiccated, grinded, and sieved to prepare microparticles of a size below 150 μm. These microparticles were weighed, and mixed with dexamethasone microparticles at a ratio of 3:7 (w/w), respectively. The mixture was compressed to prepare cylindrical granules of ϕ 0.9 mm×2 mm in size. Dexamethasone content in the prepared dexamethasone implants was 50.0%.

Thirty Kunming mice were randomized into 5 groups with 6 mice in each group. One dexamethasone implant was implanted into the medial hind leg muscle of each mouse. Samples were collected at time points as indicated in Table 8. In vivo cumulative release of dexamethasone by the implants was measured. And the results are as shown in Table 8.

TABLE 8

| | Time | | | | |
|---|---|---|---|---|---|
| | 1 day | 5 days | 10 days | 20 days | 30 days |
| Cumulative release (%) | 17.1% | 41.4% | 55.5% | 73.6% | 87.3% |
| RSD % | 42.8% | 33.3% | 17.0% | 15.3% | 11.5% |

Example 7

Fluorouracil implants prepared in Example 2 were implanted into dog peritoneum and abdominal aorta in this experiment to study: (1) local and systemic toxic effects after the implantation of fluorouracil implants; and (2) the time courses of drug concentration in the areas near the implantation sites.

Healthy adult mongrel dogs were numbered, dewormed, inspected, and weighed before the operation. Dog were fasted but allowed to have free access to water before the operation. After intraperitoneal anesthesia with 3% penotobarbital sodium solution (30 mg/kg), peritoneum was dissected near the center of the upper abdomen. 100 mg fluorouracil implants were implanted into a site near abdominal aorta, which was then labeled by using methylene blue staining. 100 mg fluorouracil implants were also implanted into sites under left and right peritoneum, respectively, wherein the sites were 5 cm away from the incision. Peritoneum was sutured thereafter.

4 dogs were sacrificed at the third day, fifth day, seventh day, and tenth day after implantation of fluorouracil implants, respectively. Implantation sites were examined for signs of hyperemia, adhesion, infection, and necrosis. Thereafter, the following samples were taken from the dogs: lymphoid tissues at various distances from implantation sites near abdominal aorta, lymphoid tissues above the left clavicle, peritoneal tissues within 0-5 cm of the peritoneal implantation sites, peripheral blood samples, and portal vain blood samples. Drug concentrations in the above samples were determined using HPLC.

No systemic toxic effects were observed during the study period. The activities of the dogs were normal, and no signs of anorexia or food refusal were observed.

Damage at implantation site: No necrosis was observed under naked eye at the implantation sites. A few cases of inflammatory cell infiltration were observed using pathological inspection.

The time courses of drug concentrations in the areas near the implantation sites are listed in Tables 9-11.

TABLE 9

Drug concentrations in peritoneal tissues near the peritoneal implantation site (μg/g)

| | | Distance from implantation site (cm) | | | | | |
|---|---|---|---|---|---|---|---|
| Time | n | 0 | 1 | 2 | 3 | 4 | 5 |
| 3 d | 4 | 52.53 ± 35.20 | 15.12 ± 11.54 | 5.32 ± 4.31 | 3.48 ± 2.74 | 2.33 ± 2.21 | 0.92 ± 0.73 |
| 5 d | 4 | 46.93 ± 37.23 | 10.40 ± 8.81 | 3.50 ± 2.73 | 2.80 ± 2.19 | 1.82 ± 1.57 | 0.71 ± 0.62 |
| 7 d | 4 | 42.64 ± 28.83 | 9.64 ± 7.63 | 2.64 ± 1.94 | 2.29 ± 1.63 | 1.48 ± 1.30 | 0.64 ± 0.44 |
| 10 d | 4 | 36.54 ± 32.31 | 5.12 ± 3.40 | 1.83 ± 1.30 | 1.71 ± 0.55 | 0.57 ± 0.22 | 0.24 ± 0.13 |

TABLE 10

Drug concentrations in lymphoid tissues near the abodominal aorta implantation site (μg/g)

| | | Distance from implantation site (cm) | | | |
|---|---|---|---|---|---|
| Time | n | 0 | 3 | 5 | 10 |
| 3 d | 4 | 48.5 ± 42.2 | 6.3 ± 4.3 | 4.3 ± 3.2 | 1.3 ± 0.6 |
| 5 d | 4 | 46.9 ± 36.3 | 5.5 ± 3.7 | 2.8 ± 0.8 | 1.0 ± 0.8 |
| 7 d | 4 | 41.6 ± 32.8 | 3.6 ± 1.9 | 1.5 ± 1.1 | 0.8 ± 0.7 |
| 10 d | 4 | 38.5 ± 24.3 | 2.0 ± 1.7 | 0.8 ± 0.2 | 0.4 ± 0.3 |

TABLE 11

Drug concentration after implantation of the controlled release fluorouracil implants (μg/g)

| | | Time (days) | | | |
|---|---|---|---|---|---|
| Sites | n | 3 | 5 | 7 | 10 |
| Peripheral blood | 4 | 0.04 ± 0.01 | 0.02 ± 0.01 | Not detected | Not detected |
| Portal vein blood | 4 | 0.6 ± 0.2 | 0.3 ± 0.18 | 0.2 ± 0.09 | 0.08 ± 0.06 |

Example 8

Preparation of lidocaine hydrochloride microparticles: 1.6 g Ethylcellulose was dissolved completely in chloroform, and mixed with 2.4 g lidocaine hydrochloride. The mixture was evaporated until dry, and the resulting solid was grinded to yield lidocaine hydrochloride microparticles of about 125 μm in size.

Preparation of lidocaine hydrochloride implants: 2.4 g octadecanol, 3.0 g lidocaine hydrochloride microparticles and 0.6 g lidocaine hydrochloride were mixed and injection molded at 65° C. Cylindrical granules about ϕ 0.9 mm×4 mm in size were prepared. The content of lidocaine hydrochloride in the lidocaine hydrochloride implant was 40.0%.

Thirty Kunming mice were randomized into 5 groups with 6 mice in each group. Two lidocaine hydrochloride implants were implanted into the medial hind leg muscle of each mouse. Samples were collected at time points as indicated in Table 12. In vivo cumulative release of lidocaine hydrochloride by the implants was measured. The results are as shown in Table 12.

TABLE 12

| | Time | | | | |
|---|---|---|---|---|---|
| | 1 day | 2 days | 3 days | 5 days | 7 days |
| Cumulative release (%) | 28.8% | 47.5% | 60.9% | 83.7% | 94.4% |
| RSD % | 30.3% | 9.6% | 15.6% | 14.1% | 8.7% |

Example 9

Preparation of methotrexate microparticles: 2.0 g Carnauba wax (melting point: 81-88° C.) and 3.0 g Methotrexate were mixed and melted at 95° C. The melted mixture was cooled and the resulting solid was grinded to yield the methotrexate microparticles of about 100 μm in size.

Preparation of methotrexate implant: 3.0 g polycaprolactone (melting point: about 62° C.) and 3.0 g methotrexate microparticles were mixed and compressed. Cylindrical granules about ϕ0.9 mm×2.0 mm in size were prepared. The content of methotrexate in the prepared methotrexate implant was 30.0%.

Thirty Kunming mice were randomized into 5 groups with 6 mice in each group. One methotrexate implant was implanted into the medial hind leg muscle of each mouse. Samples were collected at time points as indicated in Table 13. In vivo cumulative release of methotrexate by the implant was measured. The results are as shown in Table 13.

TABLE 13

|  | Time | | | | |
| --- | --- | --- | --- | --- | --- |
|  | 1 day | 5 days | 10 days | 15 days | 20 days |
| Cumulative release (%) | 18.5% | 49.9% | 69.2% | 80.0% | 90.6% |
| RSD % | 22.3% | 30.6% | 15.2% | 15.5% | 9.6% |

Example 10

Preparation of doxorubicin hydrochloride microparticles: 1.0 g Carnauba wax (melting point: about 81-88° C.) and 1.5 g doxorubicin hydrochloride were mixed and melted at 95° C. The melted mixture was cooled and the resulting solid was grinded to yield the doxorubicin hydrochloride microparticles of about 100 μm in size.

Preparation of doxorubicin hydrochloride implants: 2.0 g poly(lactide-co-glycolide) (L-lactide/glycolide=90/10, molecular weight 2.0×10$^4$, melting range: 70-79° C.) and 2.0 g doxorubicin hydrochloride microparticles were mixed and compressed. Cylindrical granules about ϕ0.9 mm×2.0 mm in size were prepared. The content of doxorubicin hydrochloride in the prepared doxorubicin hydrochloride implant was 30.0%.

Thirty Kunming mice were randomized into 5 groups with 6 mice in each group. One doxorubicin hydrochloride implant was implanted into the medial hind leg muscle of each mouse. Samples were collected at time points as indicated in Table 14. In vivo cumulative release of doxorubicin hydrochloride by the implant was measured. The results are as shown in Table 14.

TABLE 14

|  | Time | | | | |
| --- | --- | --- | --- | --- | --- |
|  | 1 day | 5 days | 10 days | 15 days | 20 days |
| Cumulative release (%) | 25.2% | 53.6% | 70.5% | 78.4% | 87.0% |
| RSD % | 27.1% | 11.8% | 20.2% | 12.7% | 4.3% |

Example 11

Preparation of gentamicin sulphate: 1.5 g Carnauba wax (melting point: 81-88° C.), and 3.5 g gentamicin sulphate were mixed and melted at 95° C. The melted mixture was cooled and the resulting solid was grinded to yield the gentamicin sulphate microparticles of about 100 μm in size.

Preparation of gentamicin sulphate implant: 2.0 g poly(lactide-co-glycolide) (L-lactide/glycolide=75/25, molecular weight 2.0×10$^4$, melting range: 68-76° C.), and 2.0 g gentamicin sulphate microparticles were mixed and compressed. Cylindrical granules about ϕ0.9 mm×2.0 mm in size were prepared. The content of gentamicin sulphate in the prepared gentamicin sulphate implant was 35.0%.

Thirty Kunming mice were randomized into 5 groups with 6 mice in each group. One gentamicin sulphate implant was implanted into the medial hind leg muscle of each mouse. Samples were collected at time points as indicated in Table 15. In vivo cumulative release of gentamicin sulphate by the implant was measured. The results are as shown in Table 15.

TABLE 15

|  | Time | | | | |
| --- | --- | --- | --- | --- | --- |
|  | 1 day | 5 days | 10 days | 15 days | 20 days |
| Cumulative release (%) | 27.1% | 56.8% | 70.0% | 85.6% | 94.3% |
| RSD % | 27.6% | 27.9% | 12.2% | 6.4% | 2.1% |

Example 12

Preparation of mycophenolate mofetil microparticles: 2.0 g poly(L-lactide) (molecular weight: 2.0×10$^4$, melting range: 162-168° C.) was dissolved in chloroform, and the solution was mixed with 3.0 g mycophenolate mofetil. Chloroform is evaporated until dry, and the resulting solid was grinded to yield mycophenolate mofetil microparticles of about 100 μm in size.

Preparation of mycophenolate mofetil implant: 2.0 g poly(CPP-SA) (CPP/SA=22/78, melting point: 66° C.), and 1.5 g mycophenolate mofetil microparticles, 0.5 g mycophenolate mofetil were mixed and extruded at 100° C. Cylindrical granules about ϕ0.9 mm×2.0 mm in size were prepared. The content of mycophenolate mofetil in the prepared mycophenolate mofetil implant was 35.0%.

Thirty Kunming mice were randomized into 5 groups with 6 mice in each group. One mycophenolate mofetil implant was implanted into the medial hind leg muscle of each mouse. Samples were collected at time points as indicated in Table 16. In vivo cumulative release of mycophenolate mofetil by the implant was measured. The results are as shown in Table 16.

TABLE 16

|  | Time | | | | |
| --- | --- | --- | --- | --- | --- |
|  | 1 day | 5 days | 10 days | 15 days | 20 days |
| Cumulative release (%) | 21.9% | 49.8% | 63.3% | 77.7% | 85.3% |
| RSD % | 15.3% | 18.1% | 8.7% | 10.0% | 1.9% |

Example 13

Preparation of fluorouracil microparticles: 80.0 g fluorouracil, 20.0 g methyl methacrylate, 0.01 g perbenzoic acid were mixed and reacted at 50-100° C. under normal pressure. The resulting mixture was cooled and grinded to yield fluorouracil microparticles of about 100 μm in size.

Preparation of fluorouracil implant: 10.0 g poly(L-lactide), 15.0 g fluorouracil microparticles were injection molded at 165° C. Cylindrical granules about ϕ0.9 mm×4.0 mm in size were prepared. The content of fluorouracil in the prepared fluorouracil implant was 47.8%.

Thirty Kunming mice were randomized into 5 groups with 6 mice in each group. One fluorouracil implant was implanted into the medial hind leg muscle of each mouse. Samples were collected at time points as indicated in Table 17. In vivo cumulative release of fluorouracil by the implant was measured. The results are as shown in Table 17.

TABLE 17

|  | Time | | | | |
| --- | --- | --- | --- | --- | --- |
|  | 1 day | 10 days | 20 days | 30 days | 40 days |
| Cumulative release (%) | 12.7% | 40.0% | 61.9% | 79.2% | 88.8% |
| RSD % | 31.3% | 31.8% | 10.7% | 5.5% | 2.3% |

Example 14

Preparation of lidocaine hydrochloride microparticles: 2.0 g poly(lactide-co-glycolide) (L-lactide/glycolide=75/25, molecular weight $2.0 \times 10^4$, melting range: 68-76° C.), 3.5 g lidocaine hydrochloride were mixed and melted at 100° C. The melted mixture was cooled and the resulting solid was grinded to yield the lidocaine hydrochloride microparticles of about 100 μm in size.

Preparation of lidocaine hydrochloride implant: 2.0 g lidocaine hydrochloride microparticles were mixed in 15 ml 15% gelatin solution, and injected into a mold. After evaporation, the resulting product was immersed in 5% glutaraldehyde solution for 1 hour, and then taken out for evaporation to prepare film sheets. The content of lidocaine hydrochloride in the prepared lidocaine hydrochloride implant was 32.1%.

The in vitro release profile was measured by static dissolution method using phosphate buffer (pH=7.4) as release medium. Samples were collected at time points as indicated in Table 18. In vivo cumulative release of lidocaine hydrochloride by the implant was measured. The results are as shown in Table 18.

TABLE 18

|  | Time | | | |
| --- | --- | --- | --- | --- |
|  | 1 day | 2 days | 3 days | 4 days |
| Cumulative release (%) | 42.2% | 68.9% | 82.5% | 95.6% |
| RSD % | 33.3% | 15.9% | 12.2% | 7.5% |

Example 15

Cisplatin implant prepared according to Example 5 was used in this study. Ascites fluid was taken from d7 H22 passage mice under sterile conditions, and the ascites fluid was diluted with normal saline to prepare tumor cell suspension at a concentration of $1.0 \times 10^7$ cells/ml. Each mouse received a subcutaneous injection of 0.2 ml tumor cell suspension at the right armpit (number of inoculated cells: $2 \times 10^6$). The mice were randomized into 6 groups the next day after inoculation, cisplatin implant or excipient control was implanted near the tumor at the seventh day after inoculation. The positive control group received an intraperitoneal injection of cisplatin the next day after inoculation, and four injections in total at an interval of twice a week. The negative control group received an intraperitoneal injection of normal saline the next day after inoculation, and four injections in total at an interval of twice a week. The mice were sacrificed at the 15th day after inoculation, and the tumor mass were peeled and weighted. Tumor growth inhibition rate was calculated using the following equation:

$$\text{tumor growth inhibition rate} = \frac{\text{tumor weight of control group} - \text{tumor weight of treated group}}{\text{tumor weight of control group}} \times 100\%$$

TABLE 19

| Group | Dose | Route of Administration | Number of animals | | Tumor weight $\overline{X} \pm$ SD (g) | Tumor growth inhibition rate (%) | P value |
| --- | --- | --- | --- | --- | --- | --- | --- |
|  |  |  | onset | end |  |  |  |
| Normal Saline | — | i.p. | 20 | 20 | 3.71 ± 1.13 | — |  |
| Excipient | — | Near the tumor | 15 | 13 | 3.67 ± 1.34 | — |  |
| cisplatin | 12 mg/kg | i.p. | 15 | 15 | 2.98 ± 1.14 | 19.68 |  |
| Cisplatin implant d7 | | | | | | | |
|  | 20 mg/kg | Near the tumor | 15 | 15 | 2.06 ± 0.73 | 43.87 | <0.05 |
|  | 10 mg/kg | Near the tumor | 15 | 15 | 2.31 ± 0.68 | 37.05 | <0.05 |
|  | 5 mg/kg | Near the tumor | 15 | 12 | 2.92 ± 0.98 | 20.43 |  |

Example 16

14 patients with non-small cell lung cancer were treated with cispatin implant prepared according to Example 5. The cisplatin implant was implanted into the tumor through CT-guided percutaneous puncture. After treatment, 3 patients showed significantly decreased disease focus, 8 patients showed stabilized disease focus, while 3 patients showed disease progression. The observed adverse effects included: nausea, vomiting, decreased appetite, lack of strength, local pain, few hemoptysis, and low-grade fever. The adverse effects generally disappeared after symptomatic treatment.

Example 17

Fluorouracil implant prepared according to Example 2 were used in this study. SGC-7901 tumor tissues at vigorous growth stage were obtained and cut into pieces of about 1.5 mm³. The tumor tissue pieces were inoculated subcutaneously to the right armpit of nude mice, under sterile conditions. The mice were randomized into 6 groups at the sixth day after inoculation. Three groups were treated with different doses of fluorouracil implant prepared according to Example 2. Another group was treated with excipient at the sixth day after noculation. The fluorouracil implant or excipient was implanted subcutaneously near the tumor. The positive group received four intraperitoneal injections of fluorouracil in total at an interval of twice a week. The negative control group received four intraperitoneal injections of normal saline in total at an interval of twice a week. The mice were sacrificed at the 21st day after inoculation, and the tumor mass were peeled and weighed. The tumor growth inhibition rate was calculated using the following equation:

$$\text{tumor growth inhibition rate} = \frac{\text{tumor weight of control group} - \text{tumor weight of treated group}}{\text{tumor weight of control group}} \times 100\%$$

etoposide implant. Each patient in Group I received a total amount of 200 mg etoposide implant under the rectal mucosa 7 days before the surgical operation. The etoposide implant was implanted into 3 channels located 1-3 cm above the rectal dentate line, and 60-70 mg etoposide implant were implanted to each channel. Group II (n=10) were treated with conventional treatment. Biopsy tissue blocks were collected from all patients prior to operation, and were used as control tissue sample for drug implanted tissue. Operation was performed 168 hours after the drug implant. After the operation, tissue blocks of about 1.0 cm×1.0 cm×0.5 cm in size were cut from tumor site and implanted site, respectively (biopsy samples were obtained from anal after operation if tissue blocks cannot be cut because of tumor fixation). The obtained tissue blocks were fixed by 10% formaldehyde solution, followed by dehydration, clarification, embedded with wax, and buried. Regular HE staining is applied to the prepared tissue slices followed by pathological analysis.

Results showed that, 14 patients in the implant group showed neither necrosis in mucosa at implant site, nor ulceration, and few bruise was observed under the mucosa. The colorectal cancer tissue slice was stained with HE and the result showed, the pathological morphology was ranked 0 degree before drug implant, after chemotherapy, 14 patients showed I-II grade change (0: no change; I grade: cancer cells swell, and the hollow vesicle denatured, the nuclears of some cancer cells condensed or dissolved, glandular tubes and cancer nests were basically not destroyed; II grade: most of the cancer cells showed significant denatur-

TABLE 20

| Group | Dose per rat | Route of Administration | Number of animals onset | Number of animals end | Tumor weight $\bar{X} \pm SD$ (g) onset | Tumor weight $\bar{X} \pm SD$ (g) end | Tumor growth inhibition rate (%) | P value | Group |
|---|---|---|---|---|---|---|---|---|---|
| NS | — | ip | 16 | 16 | 23.1 | 25.4 | 2.93 ± 0.90 | — | |
| excipient | — | Near the tumor | 8 | 8 | 23.6 | 26.2 | 2.99 ± 0.81 | — | |
| 5-FU | 1.6 mg | ip | 6 | 6 | 21.0 | 22.8 | 0.71 ± 0.42 | 75.76 | <0.01 |
| 5-FU implant d6 | | | | | | | | | |
| | 4 mg | Near the tumor | 6 | 5 | 20.7 | 21.7 | 0.02 ± 1.05 | 99.33 | <0.01 |
| | 1 mg | Near the tumor | 6 | 6 | 20.2 | 21.2 | 0.40 ± 0.37 | 86.62 | <0.01 |
| | 0.25 mg | Near the tumor | 6 | 6 | 19.9 | 22.0 | 1.27 ± 1.29 | 57.52 | <0.01 |

Example 18

24 patients with colorectal cancer were treated with etoposide implants. Etoposide implants were prepared according to Example 3. The 24 patients who were aged about 45-65 planned to do surgical operation. The pathological diagnosis of the patients was clear and indicate they were in Dukes B-C stage. The patients could tolerate to operation and chemotherapy. Consent was obtained from each patient's relative for those patient grouped into the etoposide implant treatment group.

The patients were paired according to sex, diseased area, pathological stage, and pathological type. The patients were grouped into two groups. Group I (n=14) were treated with ation, a majority of cells showed condensed nuclear or dissolved nuclear, cancer nests were detached from the glandular tubes; Ill grade: most of the cancer cells were dead, and cancer nests were dissolved and almost collapsed and disappeared.) More than ⅕ cancer cells on the slice showed spoty or pathy degeneration, and the nuclears are dissolved and condensed. The 10 patients in control group showed no obvious change in pathology before and after operation.

Before drug implant, there was no significant difference between the apoptosis index (AI, AI=(number of apoptosis cells/number of total cancer cells)×100%) and the proliferation index (PI, PI=number of PCNA positive cells/number of total cancer cells)×100%). The AI and PI did not show any significant change in non-implant group after treatment. The implant group showed increased AI and decreased PI after operation. The AI and PI of cancer tissue obtained in biopsy before drug implant were compared with the AI and PI of tissue slice after drug implant, and the results showed that the two had statistically significant difference (P<0.01).

TABLE 21

AI and PI of cancer cells from patients in Group I (n = 14) before and after drug implant (x ± s)

|  | AI | PI |
|---|---|---|
| Before implant | 1.320 ± 0.668 | 46.33 ± 11.48 |
| After implant | 3.623 ± 1.235 | 39.62 ± 16.44 |

When etoposide implants were implanted beneath the colon mucosa, the implant site did not show hemorrhage, nor obvious infection. 168 hours after the drug implant, the pathological examination on the implant site showed a few signs filtration of inflammatory cells, no necrosis was observed for colon mucosa or muscle tissues, and no ulceration, bleeding, necrosis or infection was observed at the implant site. No systemic adverse effects were observed in blood routine test, liver and renal function test, electrocardiogram tests.

Example 19

Fluorouracil implant composition prepared according to Example 2 was tested for its efficacy on pancreatic cancer. Pancreatic cancer cell line PC3 was cultured and inoculated subcutaneously to 70 nude mice at the right armpit at the dose of $2 \times 10^6$ cells per inoculation. Tumor grew to the size of about 4 mm×4 mm×4 mm 4 weeks after the implant. 60 nude mice having tumors of similar sizes were selected and randomized into 5 groups with 12 mice in each group: Group A was administered intravenously through the angular vein with normal saline at the dose of 0.1 ml per mice; Group B was administered intravenously through the angular vein with 0.1 ml fluorouracil solution in normal saline at the dose of 10 mg/kg; Group C was implanted with blank matrix; Group D was implanted with fluorouracil implant composition into the pancreatic tumor mass at the dose of 4 mg/kg; and Group E was implanted with fluorouracil implant composition into the pancreatic tumor mass at the dose of 1 mg/kg. The size of the tumor mass was measured before and after treatment. The results are shown in Table 22.

TABLE 22

Change in tumor size before and after treatment (mm³)

| Group | Before treatment | After treatment | | | |
|---|---|---|---|---|---|
| | | 3rd day | 6th day | 10th day | 14th day |
| A | 60.9 ± 8.3 | 82.2 ± 19.5 | 119.3 ± 18.4 | 147.2 ± 22.8 | 169.4 ± 12.2 |
| B | 61.5 ± 8.7 | 72.3 ± 14.6 | 96.62 ± 20.5 | 107.3 ± 20.9 | 121.6 ± 14.3 |
| C | 59.4 ± 9.2 | 83.7 ± 11.0 | 125.4 ± 14.3 | 154.7 ± 13.1 | 178.0 ± 20.2 |
| D | 60.3 ± 9.0 | 64.0 ± 13.5 | 72.8 ± 8.9 | 76.1 ± 19.2 | 82.5 ± 10.3 |
| E | 58.7 ± 8.6 | 63.1 ± 7.6 | 44.9 ± 9.0 | 81.4 ± 8.6 | 85.5 ± 12.3 |

Example 20

Mycophenolate mofetil implant composition prepared according to Example 12 was tested for its efficacy on renal inflammation.

30 female SD rats with body weigh ranging from 150 g to 170 g were randomized into 3 groups with 10 rats in each group. Each of control group, diseased group and treatment group has 10 rats. Rats in the diseased group and rats in the treatment group were both administered with one injection of doxorubicin at the dose of 7.5 mg/kg through tail vein. Rats in the control group were administered with one injection of equal volume of normal saline. The rats were fed with standard forage and allowed to free access to food and water. At the 2nd day after injection of doxorubicin, rats in the treatment group were implanted with 20 mg/kg mycophenolate mofetil implant at capsula renis at both left side and right side, and rats in the diseased group and rats in the control group were gavaged with equal volume of distilled water. Rat urine were collected for 24 hours one day before the injection of doxorubicin/normal saline, at the 14th day and the 28th day after the injection, and the protein amount was measured in the urine samples collected. If the protein amount in the urine sample collected at the 14th day was above 150 mg/24 hours, the rat was considered a successful animal model and was counted into the study. All rats were sacrificed at the 28th day after the injection, and levels of total protein (TP), albumin protein (ALB), triglyceride (TG), cholesterol (Choi), urea nitrogen (BUN), and creatinine (Cr) were measured.

TABLE 23

Amount of urine protein in the three groups of rats (mg/24 h, n = 10)

|  | Control group | Diseased group | Treatment group |
|---|---|---|---|
| 0 day | 9.98 ± 1.95 | 9.98 ± 1.67 | 10.59 ± 2.11 |
| 14th day | 11.57 ± 2.14 | 219.41 ± 15.24* | 243.89 ± 10.78 |
| 28th day | 12.87 ± 2.86 | 304.27 ± 21.04* | 168.02 ± 12.85# |

*P < 0.01 as compared with the control group;
P < 0.01 as compared with the diseased group

TABLE 24

| 28th day | TP (g/L) | ALB (g/L) | TG (mmol/L) | Chol (mmol/L) | BUN (mmol/L) | Cr (μmol/L) |
|---|---|---|---|---|---|---|
| Control group | 51.50 ± 7.82 | 30.37 ± 3.18 | 0.68 ± 0.21 | 1.58 ± 0.55 | 6.57 ± 1.68 | 57.01 ± 4.47 |
| Diseased group | 36.34 ± 5.75* | 16.55 ± 1.59* | 6.32 ± 0.76* | 8.72 ± 1.01* | 7.92 ± 1.02 | 63.28 ± 7.46 |
| Treatment group | 50.8 ± 8.62# | 33.8 ± 4.67# | 0.87 ± 0.31# | 1.68 ± 0.755# | 5.82 ± 2.38 | 69.9 ± 12.47 |

*P < 0.01 as compared with the control group;
P < 0.01 as compared with the diseased group Biochemical index of three groups of rats (n = 10)

Example 21

Gentamicin sulphate implant prepared according to Example 11 was tested for local distribution and diffusion after intramuscular implantation.

35 mongrel dogs, including 14 female dogs and 21 male dogs, were divided into 7 groups, and each group included 2 female dogs and 3 male dogs. Each dog was implanted with gentamicin sulphate implant at the biceps femoris muscle at the outer side of the right hind leg at the dose of 10 mg/kg. One group of dogs were sacrificed at a given time point, and the hind leg having implanted drug was obtained and frozen without skin. Muscle tissue samples were taken from the areas around the implantation site. X axis and Y axis were set on the muscle tissue with the origin being the implantation site. Muscle tissues were sampled along the X axis and Y axis at an interval of 10 mm. Concentrations of gentamicin sulphate in the muscle tissue samples were measured to study the distribution and diffusion of gentamicin sulphate after implantation in the muscle. The results are shown in Table 25.

TABLE 25

| | 24 h | 72 h | 120 h | 240 h | 360 h | 480 h |
|---|---|---|---|---|---|---|
| X − 3 cm | 91.16 ± 17.30 | 63.38 ± 14.90 | 47.66 ± 11.95 | 35.66 ± 9.61 | 27.56 ± 8.10 | 16.88 ± 6.63 |
| Y − 3 cm | 90.82 ± 15.29 | 63.22 ± 15.47 | 46.14 ± 10.40 | 34.84 ± 9.69 | 27.36 ± 8.68 | 17.22 ± 7.69 |
| X − 2 cm | 169.10 ± 54.87 | 109.72 ± 22.62 | 74.42 ± 14.52 | 42.40 ± 15.28 | 31.26 ± 11.55 | 26.12 ± 9.69 |
| Y − 2 cm | 167.82 ± 59.04 | 106.18 ± 22.53 | 74.88 ± 13.22 | 41.30 ± 14.43 | 30.58 ± 10.81 | 25.90 ± 8.42 |
| X − 1 cm | 304.06 ± 69.04 | 223.66 ± 54.84 | 134.62 ± 24.89 | 70.85 ± 11.34 | 46.73 ± 12.08 | 35.96 ± 8.66 |
| Y − 1 cm | 294.60 ± 71.70 | 204.46 ± 45.24 | 127.62 ± 29.63 | 71.46 ± 7.32 | 44.80 ± 13.16 | 36.54 ± 9.21 |
| 0 | 586.80 ± 56.55 | 458.74 ± 54.09 | 307.90 ± 77.54 | 113.6 ± 37.01 | 75.20 ± 24.18 | 58.30 ± 24.38 |
| Y + 1 cm | 312.58 ± 86.84 | 211.48 ± 21.33 | 136.64 ± 14.62 | 64.72 ± 11.37 | 44.66 ± 11.19 | 36.62 ± 8.19 |
| X + 1 cm | 305.12 ± 86.91 | 217.56 ± 52.20 | 135.12 ± 25.73 | 69.30 ± 8.21 | 44.48 ± 13.02 | 34.48 ± 8.51 |
| Y + 2 cm | 170.22 ± 51.72 | 111.34 ± 50.74 | 74.02 ± 14.27 | 42.84 ± 13.14 | 29.62 ± 11.14 | 24.98 ± 8.64 |
| X + 2 cm | 167.66 ± 52.48 | 110.24 ± 25.46 | 74.68 ± 16.88 | 41.06 ± 12.76 | 31.34 ± 11.31 | 27.40 ± 9.85 |
| Y + 3 cm | 89.68 ± 15.16 | 61.56 ± 15.08 | 47.80 ± 11.59 | 36.22 ± 9.73 | 27.58 ± 8.15 | 17.14 ± 6.94 |
| X + 3 cm | 89.94 ± 18.81 | 62.34 ± 15.60 | 47.60 ± 10.69 | 36.08 ± 9.16 | 29.10 ± 7.58 | 15.96 ± 7.39 |

Example 22

Lidocaine hydrochloride implant prepared according to Example 8 was administered to 10 breast cancer patients during surgical operation, where 5 patients were administered at the dose of 50 mg/patient, and 5 patients were administered at the dose of 100 mg/patient. After implantation, none of the 10 patients demonstrated sensible pain at the operation region.

Example 23

Preparation of nifedipine microparticles: 2 g ethylcellulose and 3 g nifedipine were mixed and completely dissolved in chloroform. The solvent chloroform was evaporated until dry. The resulting solid was grinded to yield microcparticles of about 90 μm in size.

Preparation of Nifedipine implant: 2 g poly(lactide-co-glycolide) (L-lactide/glycolide=90/10, molecular weight $1.6 \times 10^4$, melting temperature range: 68~76° C.), 0.3 g polyethylene glycol (4000), and 3.7 g nifedipine microparticles were mixed and compressed to prepare cylindrical granules of φ 0.9 mm×2 mm in size. Nifedipine content in the prepared nifedipine implants was 37.0%.

Thirty Kunming mice were randomized into 5 groups with 6 mice in each group. One nifedipine implant was implanted into the medial hind leg muscle of each mouse. Samples were collected at time points as indicated in Table 26. In vivo cumulative release of nifedipine by the implants was measured. And the results are as shown in Table 26.

TABLE 26

| | Time (day) | | | | |
|---|---|---|---|---|---|
| | 1 day | 5 days | 10 days | 15 days | 20 days |
| Cumulative release (%) | 16.7% | 42.3% | 63.1% | 74.9% | 83.3% |
| RSD % | 20.5% | 17.2% | 7.3% | 12.5% | 4.4% |

Example 24

Dry powders of PLGA (intrinsic viscosity: 33.40) were compressed directly into tablets and implanted subcutaneously at the back of the rat. The degradation of the implant was shown in Table 27.

TABLE 27

| Retention time in rat | Weight loss (%) | Intrinsic viscosity |
| --- | --- | --- |
| 0 day | | 33.40 |
| 1 week | 4.31 | 29.69 |
| 4 weeks | 10.17 | 23.18 |
| 6 weeks | 12.47 | 18.70 |
| 9 weeks | 25.64 | 19.26 |
| 12 weeks | 45.62 | 18.04 |
| 15 weeks | 56.51 | 17.14 |

Example 25

Dry powders of PLLA (intrinsic viscosity: 47.21) were compressed directly into tablets and implanted subcutaneously at the back of the rat. The degradation of the implant was shown in Table 28.

TABLE 28

| Retention time in rat | Weight loss (%) | Intrinsic viscosity |
| --- | --- | --- |
| 0 day | | 47.21 |
| 1 week | 3.46 | 48.38 |
| 2 weeks | 3.13 | 47.03 |
| 4 weeks | 8.46 | 43.77 |
| 12 weeks | 19.33 | 42.83 |
| 26 weeks | 27.30 | 36.51 |
| 31 weeks | 29.26 | 27.73 |
| 41 weeks | 29.26 | 25.19 |
| 46 weeks | 29.64 | 22.80 |
| 52 weeks | 43.72 | 19.91 |

Example 26

Preparation of fluorouracil microparticles: 5% silicone rubber solution was prepared using cyclohexane and used as the coating solution. Fluorouracil powders were coated and solidified for 10 times by the coating solution. The fluorouracil content in the microparticles were 94.8%.

Preparation of fluorouracil micro-implant: 5.0 g poly(L-lactide) and 9.0 g fluorouracil microparticles were mixed. Cylindrical granules about φ0.9 mm×4.0 mm in size were prepared by melt injection moulding method. The content of fluorouracil in the prepared fluorouracil implant was 60.9%.

Thirty Kunming mice were randomized into 5 groups with 6 mice in each group. One fluorouracil implant was implanted into the medial hind leg muscle of each mouse. Samples were collected at time points as indicated in Table 29. In vivo cumulative release of fluorouracil by the implants was measured. And the results are as shown in Table 29.

TABLE 29

| | Time (day) | | | | |
| --- | --- | --- | --- | --- | --- |
| | 1 day | 10 days | 30 days | 50 days | 70 days |
| Cumulative release (%) | 6.5% | 31.8% | 53.9% | 70.7% | 85.5% |
| RSD % | 37.2% | 25.1% | 19.3% | 19.1% | 10.4% |

Example 27

The release profile of fluorouracil micro-implant provided in Example 26 was compared with the release profile of the fluorouracil micro-implant prepared without the second material.

The fluorouracil micro-implant without the second material was prepared as follows: 5.0 g poly(L-lactide) and 7.8 g fluorouracil were mixed. Cylindrical granules about φ0.9 mm×4.0 mm in size were prepared by melt injection moulding method. The fluorouracil in the prepared fluorouracil implant was 60.9%.

Thirty Kunming mice were randomized into 5 groups with 6 mice in each group. One fluorouracil implant was implanted into the medial hind leg muscle of each mouse. Samples were collected at time points as indicated in Table 30. In vivo cumulative release of fluorouracil by the implants was measured. And the results are as shown in Table 30.

TABLE 30

| | Time (day) | | | | |
| --- | --- | --- | --- | --- | --- |
| | 1 day | 3 days | 5 days | 7 days | 10 days |
| Cumulative release (%) | 28.5% | 55.6% | 67.1% | 77.0% | 87.3% |
| RSD % | 42.3% | 30.3% | 10.0% | 5.1% | 1.1% |

The fluorouracil content in the fluorouracil micro-implant of Example 26 and in the fluorouracil micro-implant of Example 27 were the same, both were of 60.9% weight percentage of the implant. Therefore the percentage of released fluorouracil were compared. Table 29 shows that the implant of Example 26 released about 31% of fluorouracil after 10 days, but implant of Example 27 released about 87% of fluorouracil after 10 days as shown in Table 30. The implant of Example 26 continued to release fluorouracil even 70 days after the implantation. The results showed that fluorouracil implant of Example 26 demonstrated a significantly longer release period than that achieved by the implant of Example 27.

Example 28

Preparation of gentamicin sulphate microparticles: 3.0 g Carnauba wax (melting temperature range: 81-88° C.) and 7.0 g gentamicin sulphate were mixed and melted at 95° C. The melted mixture was cooled and the resulting solid was grinded to yield the gentamicin sulphate microparticles of about 100 μm in size.

Preparation of gentamicin sulphate implant: 7.2 g (L-lactide-glycolide) (L-lactide/glycolide=75/25, molecular weight $2.0 \times 10^4$, melting temperature range 68-76° C.), 8.0 g gentamicin sulphate microparticles and 8.0 g stearyl alcohol were mixed. The mixed powders were compressed directly into tablets to prepare gentamicin sulphate implant. The gentamicin sulphate content in the gentamicin sulphate implant was 35.0%.

Thirty Kunming mice were randomized into 5 groups with 6 mice in each group. One gentamicin sulphate implant was implanted into the medial hind leg muscle of each mouse. Samples were collected at time points as indicated in Table 31. In vivo cumulative release of gentamicin sulphate by the implants was measured. And the results are as shown in Table 31.

TABLE 31

| | Time (day) | | | | |
|---|---|---|---|---|---|
| | 1 day | 5 days | 10 days | 15 days | 20 days |
| Cumulative release (%) | 21.1% | 50.5% | 63.9% | 76.7% | 85.5% |
| RSD % | 22.7% | 8.2% | 11.3% | 10.1% | 2.4% |

Example 29

6 mongrel dogs, including 3 females and 3 males, were dewormed and fasted for 12 hours. Each dog was implanted with gentamicin sulphate implant at the biceps femoris muscle at the outer side of the right hind leg at the dose of 20 mg/kg. Blood samples were drawn from the peripheral veins at given time points and placed in tubes coated with anticoagulant. The concentration of gentamicin sulphate in the blood samples were measured and the results were shown in Table 32.

TABLE 32

| Time (Hour) | Concentration (µg/ml) | RSD % |
|---|---|---|
| 2 | 2.80 | 1.96 |
| 4 | 1.96 | 2.94 |
| 6 | 1.18 | 4.91 |
| 8 | 1.07 | 5.19 |
| 12 | 0.86 | 6.24 |
| 24 | 0.72 | 7.66 |
| 48 | 0.60 | 8.63 |
| 72 | 0.48 | 10.87 |
| 96 | 0.42 | 11.95 |
| 120 | 0.33 | 17.35 |
| 168 | 0.26 | 19.46 |
| 216 | 0.17 | 35.68 |
| 240 | 0.13 | 38.00 |
| 312 | 0.07 | 71.47 |

6 mongrel dogs, including 3 females and 3 males, were dewormed and fasted for 12 hours. Each dog was injected with gentamicin sulphate injection at the biceps femoris muscle at the outer side of the right hind leg at the dose of 20 mg/kg. Blood samples were drawn from the peripheral veins at given time points and placed in tubes coated with anticoagulant. The concentration of gentamicin sulphate in the blood samples were measured and the results were shown in Table 33.

TABLE 33

| Time | Concentration (µg/ml) | RSD % |
|---|---|---|
| 5 min | 11.35 | 11.70 |
| 10 min | 15.61 | 8.62 |
| 15 min | 19.60 | 7.09 |
| 30 min | 25.17 | 4.95 |
| 45 min | 31.73 | 4.14 |
| 1 h | 40.73 | 3.11 |
| 1.5 h | 35.39 | 3.84 |
| 2 h | 31.77 | 4.15 |
| 3 h | 26.69 | 4.85 |
| 4 h | 13.58 | 9.08 |
| 8 h | 3.76 | 32.62 |
| 16 h | 0.52 | 91.49 |
| 24 h | <0.02 | N/A |

While the invention has been disclosed in its preferred forms, it will be apparent to those skilled in the art that many modifications, additions, and deletions can be made therein without departing from the spirit and scope of the invention and its equivalents as set forth in the following claims.

What is claimed is:

1. A method for making a controlled release implantable pharmaceutical composition comprising the steps of:
preparing a plurality of microparticles comprising a first material and a first active agent;
applying the plurality of microparticles to a matrix-forming composition comprising a second material to form a mixture;
heating the matrix-forming composition to a temperature $T_m$ wherein $T_H > T_m > T_L$, and wherein the matrix-forming composition is liquefied while the microparticles do not liquefy, and
cooling down to form the controlled release implantable pharmaceutical composition comprising the plurality of said microparticles distributed or embedded in the second material, wherein:
the microparticles have a diameter ranging from about 120 um to about 100 um;
the first material comprises an initial melting temperature $T_H$;
the second material comprises a complete melting temperature $T_L$;

$$\Delta T = T_H - T_L;$$

$$\Delta T > 0;$$

the second material degrades faster than the first material; and
the first material is poly(L-lactide acid), and the second material is pol(lactide-co-glycolide acid).

2. The method of claim 1, wherein $T_H - T_m$ and/or $T_m - T_L$ is ≥ about 5° C.

3. The method of claim 1, wherein $T_m$ is in a range of $(T_H + T_L)/2 \pm$ about 20° C.

4. The method of claim 1, further comprising providing a coating to the controlled release implantable pharmaceutical composition.

5. The method of claim 1, wherein the controlled release implantable pharmaceutical composition is formed by using a method selected from the group consisting of: extrusion method, extrusion moulding method, injection molding method, compression moulding method, casting method, coating method, and calendaring method.

6. The method of claim 1, wherein the matrix-forming composition comprises a second active agent.

7. The method of claim 6, wherein the first active agent or the second active agent is independently selected from the group consisting of: local anesthetics, antiepileptic drugs and anticonvulsants, anti-alzheimer's disease drugs, analgesics, antipodagric, anti-hypertensive drugs, antiarrhythmic drugs, diuretic drugs, drugs for treating liver diseases, drugs for treating pancreatic diseases, antihistamine drugs, anti-allergic drugs, glucocorticoid drugs, sex hormone drugs and contraceptive drugs, hypoglycemic drugs, anti-osteoporosis drugs, antibiotics, sulfonamides, quinolones, and other synthetic antibacterial drugs, antituberculous drugs, antiviral drugs, anti-neoplasm drugs, immunomodulators, and cosmetically active agents.

8. The method of claim 1, wherein the microparticles comprise a weight percentage of about 2% to about 98% of the first material, and about 2% to about 98% of the first active agent.

9. The method of claim 1, wherein the controlled release implantable pharmaceutical composition comprises about 1% to about 95% of the microparticles.

10. The method of claim 1, wherein the plurality of microparticles are uniformly distributed or embedded in the matrix-forming composition.

11. The method of claim 1, wherein the plurality of microparticles are distributed or embedded in the matrix-forming composition in accordance with a pre-determined pattern.

12. The method of claim 1, wherein at least one of the plurality of the microparticles further comprises a coating.

13. The method of claim 1, wherein the microparticles further comprise a first additive.

* * * * *